United States Patent
Yang et al.

(10) Patent No.: US 10,586,355 B2
(45) Date of Patent: *Mar. 10, 2020

(54) IMAGE RECONSTRUCTION SYSTEM AND METHOD

(71) Applicant: SHANGHAI UNITED IMAGING HEALTHCARE CO., LTD., Shanghai (CN)

(72) Inventors: Le Yang, Shanghai (CN); Haihua Zhou, Shanghai (CN); Juan Feng, Shanghai (CN); Kai Cui, Shanghai (CN); Ji Qi, Shanghai (CN); Na Zhang, Shanghai (CN); Hao Chen, Shanghai (CN); Jie Niu, Shanghai (CN); Yecheng Han, Shanghai (CN); Wanli Teng, Shanghai (CN); Yange Ma, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/199,025

(22) Filed: Nov. 23, 2018

(65) Prior Publication Data

US 2019/0108661 A1    Apr. 11, 2019

Related U.S. Application Data

(63) Continuation of application No. 15/317,382, filed as application No. PCT/CN2016/099061 on Sep. 14, 2016, now Pat. No. 10,140,735.

(30) Foreign Application Priority Data

Sep. 15, 2015 (CN) .......................... 2015 1 0583366
Sep. 15, 2015 (CN) .......................... 2015 1 0583397
Jan. 29, 2016 (CN) .......................... 2016 1 0066684

(51) Int. Cl.
  *G06K 9/00* (2006.01)
  *H05G 1/70* (2006.01)
  (Continued)

(52) U.S. Cl.
  CPC .......... *G06T 11/008* (2013.01); *A61B 5/0095* (2013.01); *A61B 5/015* (2013.01);
  (Continued)

(58) Field of Classification Search
  USPC ........ 382/100, 103, 106–107, 128–134, 153, 382/162, 168, 173, 181, 199, 209, 232,
  (Continued)

(56) References Cited

U.S. PATENT DOCUMENTS 7,366,277 B2    4/2008 Goto et al.
7,974,490 B2 *  7/2011 Lee .......................... G06T 5/003
                                                                382/263

(Continued)

FOREIGN PATENT DOCUMENTS

CN    1236728 C    1/2006
CN    103559695 A   2/2014
(Continued)

OTHER PUBLICATIONS

First Office Action in Chinese Application No. 201510583366.0 dated May 16, 2017, 11 pages.
(Continued)

*Primary Examiner* — Seyed H Azarian
(74) *Attorney, Agent, or Firm* — Metis IP LLC

(57) ABSTRACT

A method and system for image reconstruction are provided. A projection image of a projection object may be obtained. A processed projection image may be generated based on the projection image through one or more pre-process opera-
(Continued)

tions. A reconstructed image including an artifact may be reconstructed based on the processed projection image. The artifact may be a detector edge artifact, a projection object edge artifact, and a serrated artifact. The detector edge artifact, the projection object edge artifact, and the serrated artifact may be removed from the reconstructed image.

20 Claims, 24 Drawing Sheets

(51) Int. Cl.
| | |
|---|---|
| G06T 11/00 | (2006.01) |
| A61B 6/02 | (2006.01) |
| A61B 6/00 | (2006.01) |
| G06T 7/13 | (2017.01) |
| G06T 7/174 | (2017.01) |
| A61B 5/00 | (2006.01) |
| A61B 5/01 | (2006.01) |
| A61B 5/026 | (2006.01) |
| A61B 6/03 | (2006.01) |
| A61B 8/08 | (2006.01) |
| G06K 9/46 | (2006.01) |

(52) U.S. Cl.
CPC ............ *A61B 5/0263* (2013.01); *A61B 6/025* (2013.01); *A61B 6/032* (2013.01); *A61B 6/037* (2013.01); *A61B 6/502* (2013.01); *A61B 6/504* (2013.01); *A61B 6/5205* (2013.01); *A61B 6/5258* (2013.01); *A61B 8/0883* (2013.01); *A61B 8/485* (2013.01); *G06K 9/4633* (2013.01); *G06K 9/4638* (2013.01); *G06T 7/13* (2017.01); *G06T 7/174* (2017.01); *G06T 11/005* (2013.01); *G06T 11/006* (2013.01); *G06T 2207/10081* (2013.01); *G06T 2207/20156* (2013.01); *G06T 2207/30068* (2013.01); *G06T 2211/421* (2013.01)

(58) Field of Classification Search
USPC ........ 382/254, 260, 264, 274–276, 286–291, 382/263, 305; 378/4, 21, 23, 92
See application file for complete search history.

(56) References Cited

U.S. PATENT DOCUMENTS

| 8,655,033 | B2 | 2/2014 | Zeng et al. | |
|---|---|---|---|---|
| 9,392,986 | B2 | 7/2016 | Ning et al. | |
| 9,437,017 | B2 | 9/2016 | Dong et al. | |
| 2004/0202280 | A1 | 10/2004 | Besson | |
| 2005/0123089 | A1 | 6/2005 | De Man | |
| 2005/0135664 | A1* | 6/2005 | Kaufhold | G06T 11/006 382/131 |
| 2005/0147320 | A1 | 7/2005 | Hsieh et al. | |
| 2007/0165769 | A1 | 7/2007 | Goto et al. | |
| 2007/0183641 | A1 | 8/2007 | Peters et al. | |
| 2008/0008372 | A1 | 1/2008 | Li et al. | |
| 2008/0267470 | A1 | 10/2008 | Zhang et al. | |
| 2009/0022264 | A1 | 1/2009 | Zhou et al. | |
| 2009/0304256 | A1 | 12/2009 | Palma et al. | |
| 2011/0038516 | A1* | 2/2011 | Koehler | G06T 7/149 382/128 |
| 2011/0097007 | A1* | 4/2011 | Zeng | G06T 11/006 382/260 |
| 2013/0094735 | A1 | 4/2013 | Zamyatin et al. | |
| 2014/0016847 | A1* | 1/2014 | Nett | G06T 11/008 382/131 |
| 2015/0228092 | A1 | 8/2015 | Claus | |
| 2016/0007948 | A1 | 1/2016 | Isola et al. | |
| 2016/0012615 | A1 | 1/2016 | Gao et al. | |
| 2017/0020474 | A1 | 1/2017 | Ning et al. | |

FOREIGN PATENT DOCUMENTS

| CN | 102768759 B | 11/2014 |
|---|---|---|
| CN | 102800073 B | 1/2015 |
| CN | 104794744 A | 7/2015 |
| CN | 105078492 A | 11/2015 |
| CN | 105184835 A | 12/2015 |
| CN | 105761217 A | 7/2016 |
| CN | 103186886 B | 4/2017 |

OTHER PUBLICATIONS

First Office Action in Chinese Application No. 201510583397.6 dated Jul. 5, 2017, 12 pages.
First Office Action in Chinese Application No. 201610066684.4 dated Apr. 21, 2017, 11 pages.
International Search Report for PCT/CN2016/099061 dated Nov. 30, 2016, 5 pages.
Written Opinion of the International Search Authority for PCT/CN2016/099061 dated Nov. 30, 2016, 5 pages.
Jia Xiling, A New Algorithm of Edge Detection Based on Two-value Image, Sci-Tech Information Development & Economy, 19(4): 122-123, 2009.
Yao Lu et al., A Diffusion-based Truncated Projection Artifact Reduction Method for Iterative Digital Breast Tomosynthesis Reconstruction, Physics in Medicine and Biology, 58(3): 569-587, 2013.
Zhang Yiheng et al., Artifact Reduction Methods for Truncated Projections in Iterative Breast Tomosynthesis Reconstruction, J Comput Assist Tomogr, 33(3): 426-435, 2009.
K. Bliznakova et al., Comparison of Algorithms for Out-of-plane Artifacts Removal in Digital Tomosynthesis Reconstructions, Computer Methods and Programs in Biomedicine, 7: 75-83, 2012.
Yao Lu et at., Improving Image Quality of Digital Breast Tomosynthesis by Artifact Reduction, IWDM, 7361: 745-752, 2012.
Loannis Sechoioulos, A Review of Breast Tomosynthesis. Part II. Image Reconstruction, Processing and Analysis, and Advanced Applications, Med. Phys., 40(1): 014302-1-17. 2013.

* cited by examiner

IMAGE RECONSTRUCTION SYSTEM AND METHOD

CROSS-REFERENCE TO RELATED APPLICATIONS

This application is a continuation of U.S. application Ser. No. 15/317,382, filed on Dec. 8, 2016, which is a U.S. national stage entry of International Application No. PCT/CN2016/099061, filed on Sep. 14, 2016, which in turn claims priority of Chinese Patent Application No. 201510583366.0 filed on Sep. 15, 2015, Chinese Patent Application No. 201510583397.6 filed on Sep. 15, 2015, and Chinese Patent Application No. 201610066684.4 filed on Jan. 29, 2016, the entire contents of each of which are hereby incorporated by reference.

TECHNICAL FIELD

The present disclosure generally relates to image processing, and more particularly, to a system and method for image reconstruction.

BACKGROUND

Imaging reconstruction techniques are widely used in disease diagnosis. However, reconstructed images may include a variety of artifacts, which may cause misdiagnose. Thus, it may be desirable to develop an image reconstruction method and system that may remove or reduce artifacts to improve the quality of reconstructed image.

SUMMARY

The present disclosure relates to image processing. One aspect of the present disclosure relates to a method for image reconstruction. The method may include one or more of the following operations. A projection image of a projection object may be obtained. A processed projection image may be generated according to one or more pre-processing operations on the projection image. For example, the pre-processing the projection image may include segmenting the projection image to generate a segmented projection image. A reconstructed image including an artifact may be generated based on the processed projection image. The artifact may be removed in the reconstructed image.

In some embodiments, the pre-processing the projection image may further include generating a negative film of the segmented projection image, and correcting a geometrical error of the negative film of the segmented projection image.

In some embodiments, the reconstructing the processed projection image to generate the reconstructed image may include filtering the processed projection image to generate a filtered projection image including a highlighted artifact and an X-ray attenuation artifact, correcting the highlighted artifact and the X-ray attenuation artifact in the filtered projection image to generate a first image, and performing back projection to generate the reconstructed image based on the first image.

In some embodiments, the artifact may include a detector edge artifact relating to a detector edge, a projection object edge artifact relating to a projection object edge, and a serrated artifact.

In some embodiments, the detector edge artifact, the projection object edge artifact, and the serrated artifact may be removed in the reconstructed image.

In some embodiments, the reconstructed image may include a tomographic image.

In some embodiments, the removing serrated artifact in a tomographic image may include one or more of the following operations. A mapping position of the detector edge in the tomographic image may be determined. A projection object edge in the tomographic image may be determined. An intersection point corresponding to the projection object edge and the mapping position of the detector edge may be determined. Dislocation information of the intersection point based on the intersection point and the serrated artifact may be determined. The serrated artifact may be removed based on the intersection point and the dislocation information of the intersection point.

In some embodiments, the determining a mapping position of the detector edge in the tomographic image may include one or more of the following operations. A first geometric position relationship between a radiation source and the detector may be determined. A second geometric position relationship between the projection image and the tomographic image may be determined. Mapping coordinates of pixels in the projection image based on the first geometric position relationship and the second geometric position relationship may be determined. The mapping position of the detector edge based on the mapping coordinates of pixels in the projection image and an imaging area of the detector in projection image may be determined.

In some embodiments, the dislocation information of the intersection point is a horizontal distance between the intersection point and a point on an edge of the serrated artifact.

In some embodiments, the removing the serrated artifact based on the intersection point and the dislocation information of the intersection point may include one or more of the following operations. A projection object template of the tomographic image may be created. The serrated artifact may be removed in the projection object template to obtain a corrected projection object templet. The serrated artifact may be removed in the tomographic image based on the corrected projection object template.

In some embodiments, the segmenting the projection image to generate a segmented projection image may include one or more of the following operations. An average gray value of one or more pixels of the projection image may be determined. For each pixel of the one or more pixels of the projection image, mark A or mark B may be assigned to the pixel based on a relationship between a gray value of the pixel and the average gray value. A boundary of a region of interest based on the assigned mark of each pixel of the one or more pixels of the projection image may be determined.

In some embodiments, the boundary of the region of interest may be determined based on a seed filling algorithm.

Another aspect of the present disclosure relates to a non-transitory computer readable medium including executable instructions. The instructions, when executed by at least one processor, may cause the at least one processor to effectuate a method for image reconstruction. In some embodiments, the non-transitory computer readable medium may include instructions for causing a computer to implement the method described herein.

A further aspect of the present disclosure relates to a system for image reconstruction. The system may include a pre-procession module to pre-process a projection image to generate a processed projection image. In some embodiments, the pre-procession module may include a segmentation unit, a negative film unit, and a geometrical error correction unit. The system may further include a reconstruction module to reconstruct the processed projection image to generate a reconstructed image including an artifact. In some embodiments, the artifact may be a detector edge artifact relating to a detector edge, a projection object edge artifact relating to a projection object edge, and a serrated artifact. The system may further include an artifact removal module to remove the artifact.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
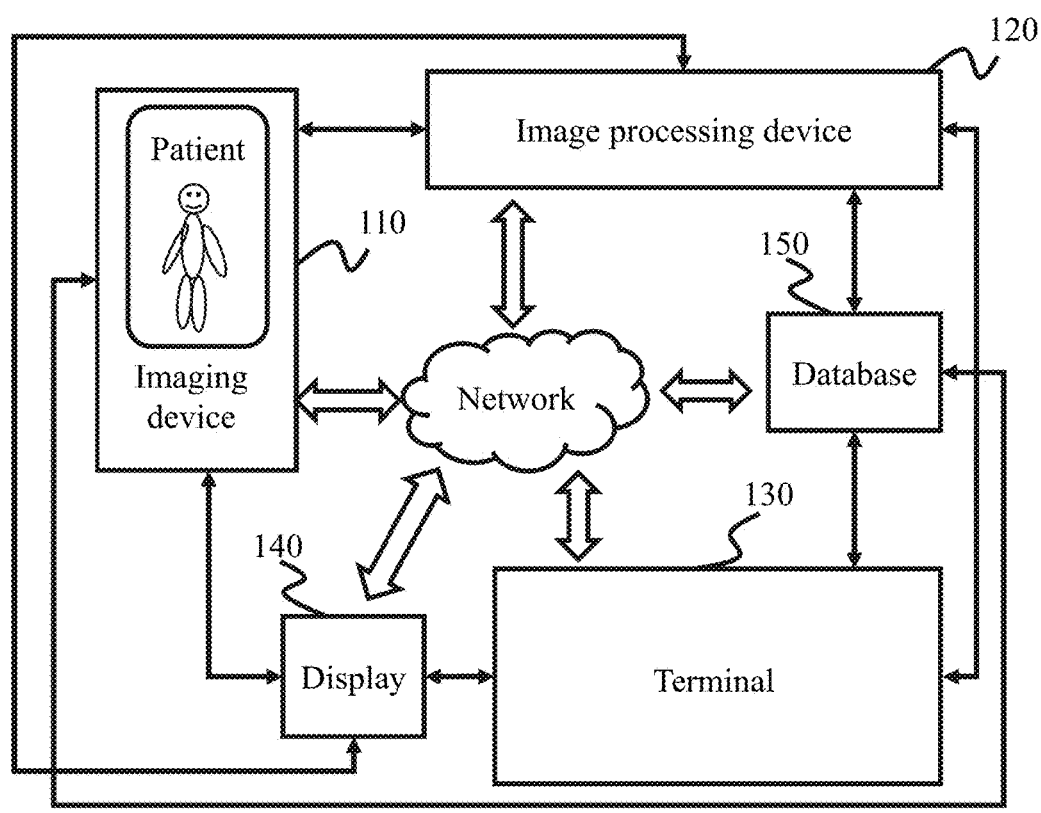
FIG. 1 illustrates a schematic diagram of an image reconstruction system 100 according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

The present disclosure provided herein relates to an image reconstruction system. Specifically, the present disclosure relates to a system and method for reconstructing image. According to some embodiments of the present disclosure, the method may include pre-processing a projection image to generate a processed projection image. The pre-processing a projection image may include segmenting the projection image to generate a segmented projection image. The processed projection image may be reconstructed to generate a reconstructed image including an artifact. The method may further include removing the artifact in the reconstructed image. The removing the artifact in the reconstructed image including removing a detector edge artifact, removing a projection object edge artifact, and removing a serrated artifact.

FIG. 1 illustrates a schematic diagram of an image reconstruction system 100 according to some embodiments of the present disclosure. Image reconstruction system 100 may include an imaging device 110, an image processing device 120, a terminal 130, a display 140, a database 150, and a network 160. In some embodiments, at least part of image processing device 120 may be implemented on computer 200 shown in FIG. 2B.

Imaging device 110 may obtain an image. The image may be a three-dimensional (3D) image, a two-dimensional (2D) image, or the like, or a combination thereof. The image may be a projection image, a re-projection image, or the like, or a combination thereof. The image may be a digital breast tomosynthesis (DBT) image, a full-field digital mammography system (FFDM) image, and a magnetic resonance (MR) image, or the like, or a combination thereof. The image may be an image of an object. For example, the image may be a 3D projection image of a mammary gland. The image may be a 2D projection image of a mammary gland. In some embodiments, a 3D image may correspond to a stack of 2D images. A 2D image may be referred to as a tomographic image or a slice image. For instance, a 3D digital image of a mammary gland may correspond to a stack of 2D tomographic images of the mammary gland.

Imaging device 110 may utilize various imaging techniques. The imaging technique may be a non-invasive imaging technique or an invasive imaging technique. The technique may be based on or relate to radiography (e.g., fluoroscopy projection radiography, etc.), magnetic resonance imaging (MRI), nuclear medicine (e.g., scintigraphy, single-photon emission computerized tomography (SPECT), positron emission tomography (PET), etc.), ultrasound (e.g., ultrasound scanning (US), etc.), elastography (e.g., quasistatic elastography/strain imaging, shear wave elasticity imaging (SWEI), acoustic radiation force impulse imaging (ARFI), supersonic shear imaging (SSI), and transient elastography, etc.), tactile imaging, photoacoustic imaging, thermography, tomography, conventional tomography, computer-assisted tomography (e.g., X-ray computed tomography (CT), positron emission tomography (PET), magnetic resonance imaging (MM), etc.), echocardiography, functional near-infrared spectroscopy (FNIR), digital subtraction angiography (DSA), computed tomography angiography (CTA), digital radiation (DR), magnetic resonance angiography (MRA), or the like, or a combination thereof.

In some embodiments, imaging device 110 may include an X-radiation source and a radiation detector (not shown in FIG. 1). Imaging device 110 may use a low dose X-ray to create a three-dimensional image of the breast. For example, imaging device 110 may be a digital breast tomosynthesis (DBT) shown in FIG. 2A.

Image processing device 120 may process an image. For example, image processing device 120 may reconstruct an image to generate a reconstructed image, enhance an image to generate an enhanced image, extract some information from an image, remove artifact of an image, or the like, or a combination thereof. The image may be obtained by imaging device 110 or retrieved from another source (e.g., database 150, a storage, etc.). The reconstructed image may include one or more tomographic images. For example, image processing device 120 may reconstruct a 3D tomographic image of a mammary gland based on one or more mammary gland projection images obtained by imaging device 110.

Image processing device 120 may be any kind of device that may process an image. For example, image processing device 120 may include a high-performance computer specialized in image processing or transaction processing, a personal computer, a portable device, a server, a microprocessor, an integrated chip, a digital signal processor (DSP), a pad, a PDA, or the like, or a combination thereof. In some embodiments, imaging processing device 120 may be implemented on computer 200 shown in FIG. 2B.

Image processing may include performing one or more operations on the image. The operations may include image manipulation (e.g., rotating, flipping, resizing, cropping, etc.), image segmentation, image reconstruction, image filtering, image binarization, image overlapping, image matching, image negative film, image artifact removing, color correction, geometric transformation, image noise reduction, image enhancement, image compression, or the like, or a combination thereof. In some embodiments, image processing device 120 may segment image to get a region of interest, and perform image reconstruction operation on the region of interest.

Methods used in image processing may include an image reconstruction method, an image segmentation method, an image binarization method, an image artifact removing method, or the like, or a combine thereof. As used herein, "removing" artifact may refer to completely or partially remove artifact that is present or identified by an image processing technology or method.

Image reconstruction methods may include filtered back projection (FBP), the simultaneous iterative reconstruction technique (SIRT), matrix inversion tomosynthesis (MITS), iterative maximum a posteriori statistical reconstruction, Bayesian-based interactive reconstruction, or the like, or a combination thereof. More descriptions regarding a filtered back projection may be found elsewhere in the present disclosure. See, for example, FIG. 4 and FIG. 8, and the description thereof.

Image segmentation methods may include an edge detecting method, a threshold segmenting method, a histogram-based method, a clustering method, a compression-based method, a region-growing method, a graph partitioning method, or the like, or a combination thereof. More details descriptions regarding region-growing method may be found elsewhere in the present disclosure. See, for example, FIG. 6 and FIG. 7, and the description thereof.

Image artifact removing methods may include a polynomial interpolation method, an iterative deblurring method, an expectation-maximization method, an algebraic reconstruction technique, a Markov random field method, a wavelet method, an ordered subsets convex iterative method, a beam-stop technique, a scanning lead-strip technique, or the like, or a combination thereof. More details descriptions regarding image artifact removing methods may be found elsewhere in the present disclosure. See, for example, FIG. 10 and FIG. 11, and the description thereof.

Terminal 130 may be connected to or communicate with image processing device 120 and allow one or more operators to control the production and/or display of images on display 140. Terminal 130 may include an input device, an output device, a control panel (not shown in figure), or the like, or a combination thereof The input device may be a keyboard, a touch screen, a mouse, a remote controller, a wearable device, or the like, or a combination thereof. An input device may include alphanumeric and other keys that may be inputted via a keyboard, a touch screen (e.g., with haptics or tactile feedback), a speech input, an eye tracking input, a brain monitoring system, or any other comparable input mechanism. The input information received through the input device may be communicated to image processing device 120 via network 160 for further processing. Another type of the input device may include a cursor control device, such as a mouse, a trackball, or cursor direction keys to communicate direction information and command selections to, for example, image processing device 120 and to control cursor movement on display 140 or another display device.

Display 140 may display information. The information may include an image before and/or after image processing, a request for input or parameter relating to image acquisition and/or processing, or the like, or a combination thereof. The display device may include a liquid crystal display (LCD), a light emitting diode (LED)-based display, a flat panel display or curved screen (or television), a cathode ray tube (CRT), or the like, or a combination thereof.

Database 150 may store images and/or relevant information or parameters. Exemplary parameters may include the coordinate of the radiation source, the radiation angle of the radiation source, the coordinate of the rotating center of the radiation source, the pixel size of a projection image, the width of a projection image, the height of a projection image, the coordinate vector of a pixel in a projection image, the width of a reconstructed image, the height of a reconstructed image, the pixel size of a reconstructed image, the coordinate vector of a pixel in a reconstructed image, or the like, or a combination thereof.

Network 160 may establish connection between different units in system 100. Network 160 may be a single network, or a combination of various networks. Network 160 may be a wired network or a wireless network. The wired network may include using a Local Area Network (LAN), a Wide Area Network (WAN), a Bluetooth, a ZigBee, a Near Field Communication (NFC), or the like, or a combination thereof. The wireless network may be a Bluetooth, a Near Field Communication (NFC), a wireless local area network (WLAN), WiFi, a Wireless Wide Area Network (WWAN), or the like, or a combination thereof.

It should be noted that the descriptions above in relation to image reconstruction system 100 is provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. For example, part or all of the image obtained by imaging device 110 may be processed by terminal 130. In some embodiments, imaging device 110 may pre-process the obtained image, before the image data is sent to the image processing device 120 for further processing. In some embodiments, terminal 130 and display 140 may be combined with image processing device 120 as single device. Similar modifications should fall within the scope of the present disclosure.

Figure 2A:
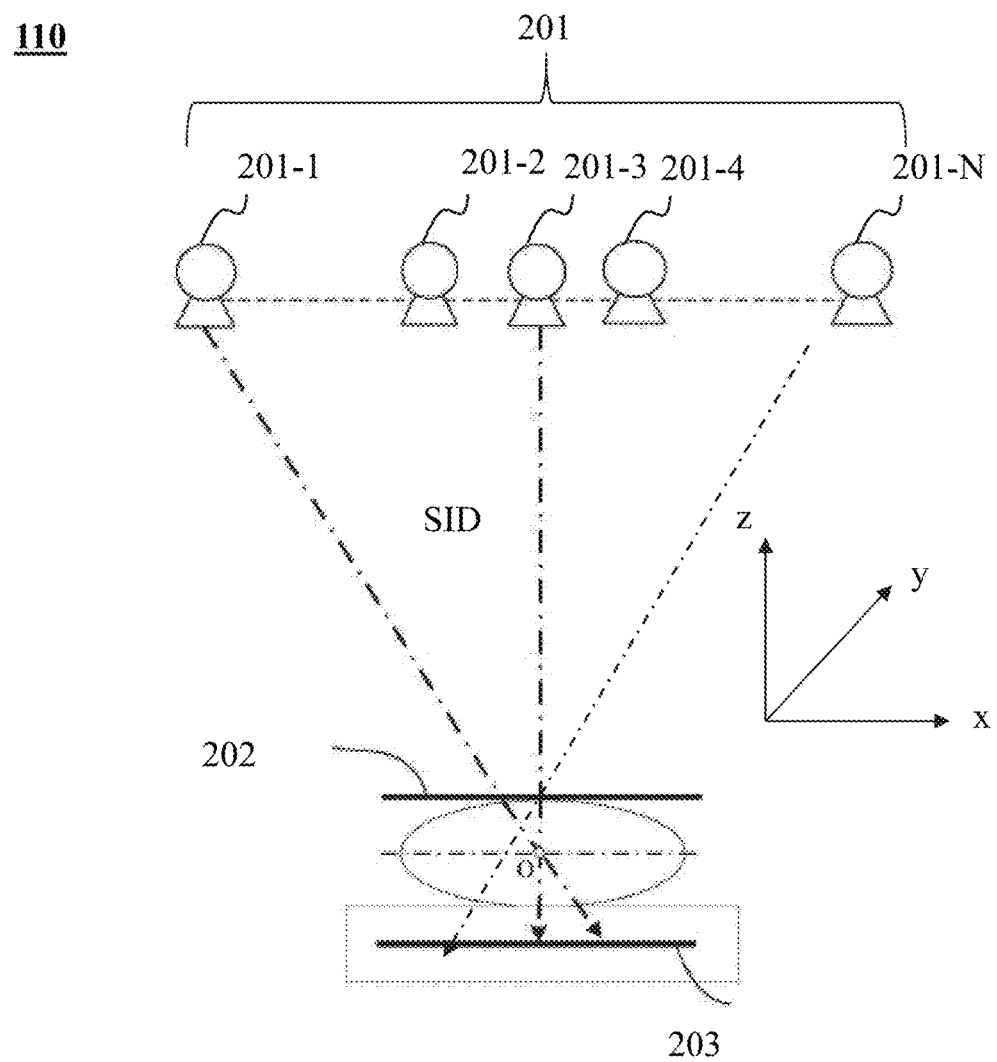
FIG. 2A illustrates an exemplary imaging device according to some embodiments of the present disclosure.

FIG. 2A illustrates an exemplary imaging device 110 according to some embodiments of the present disclosure. Imaging device 110 may obtain a projection image of a projection object. The projection object may be an organism, and an organ (e.g., a mammary gland, a hand, a head, a lung, etc.), or the like, or a combination thereof. The projection image may be further processed by imaging processing device 120 (shown in FIG. 1 and FIG. 3A) or computer 200 (shown in FIG. 2B). Imaging device 110 may include a radiation source 201, a detector 203, and a compression plate 202.

Radiation source 201 may emit radiation. The radiation may be electromagnetic radiation (e.g., X-ray, gamma radiation, visible light, etc.), particle radiation (e.g., alpha radiation, beta radiation, neutron radiation, etc.), acoustic radiation (e.g., ultrasound), gravitational radiation, or the like, or a combination thereof. In some embodiments, radiation source 201 may be an X-ray source. In some embodiments, radiation source 201 may be configured as a bulb that may emit X-radiation.

Radiation source 201 may include an even number (e.g., two, four, eight, sixteen, thirty, etc.) of sub-sources, or an odd number (e.g., one, three, five, thirty-one, etc.) of subsources. As used herein, a sub-source (illustrated as 201-1 through 201-N in FIG. 2A) of radiation source 201 may include a device or a structural component that may emit radiation. For instance, a sub-source may include a bulb that may emit radiation. In some embodiments, the number of sub-sources of radiation source 201 may be one. In some embodiments, the number of sub-sources of radiation source 201 may be more than one. At least two of a plurality of sub-sources of radiation sources 201 may be the same or different in type (e.g., X-ray source, gamma radiation source, etc.). At least two sub-sources of radiation source 201 may have the same or different characteristic parameter(s) (e.g., volume, shape, power, tube current, geometric magnification, total magnification, focus port size, radiation protection, etc.).

Merely by way of example, radiation sub-sources 201-1 through 201-4 may provide X-ray radiation, and radiation sub-source 201-N may provide gamma radiation. In some embodiments, the power of radiation sub-source 201-1 may be 3 W, and the power of radiation sub-sources 201-2 through 201-N may be 5 W. A source to image-receptor distance (SID) may be any length (e.g., 0.5 m, 0.8 m, 1.0 m, 1.5 m, etc.). As used herein, SID may refer to a distance between radiation source 201 and a projection image-receptor (e.g., detector 203, etc.). If radiation source 201 includes a plurality of sub-sources, SID may refer to a distance between a sub-source of radiation source 201 and a projection image-receptor (e.g., detector 203, etc.). The SID of sub-sources 201-1 through 201-N may be the same or different.

In some embodiments, radiation sub-sources 201-1 through 201-N may be arranged in a straight line. The distances between two neighboring radiation sub-sources 201 may be the same or different. In some embodiments, all of radiation sub-sources 201-1 through 201-N may be arranged in a same line and the distances between each two neighboring radiation sub-sources (e.g., between radiation sub-source 201-1 and radiation sub-source 201-2, between radiation sub-source 201-2 and radiation sub-source 201-3, between radiation sub-source 201-3 and radiation sub-source 201-4, etc.) may be the same. In some embodiments, radiation sub-sources 201-1 through 201-N may be arranged in a curved line, and at least two arc lengths between neighboring radiation sub-sources (e.g., between radiation sub-source 201-1 and radiation sub-source 201-2, radiation sub-source 201-2 and radiation sub-source 201-3, etc.) are the same or different.

In some embodiments, radiation source 201 may be arranged in a whole or a part of circle with projection object (e.g., a mammary gland) at the center of the circle.

The location of one or more radiation sub-sources 201-1 through 201-N may be fixed or movable. In some embodiments, the location of one or more radiation sub-sources 201-1 through 201-N may be fixed as described above. In some embodiments, the location of one or more radiation sub-sources 201-1 through 201-N may be changed according to the configurations of image reconstruction system 100. For example, radiation source 201 (or a radiation sub-source) may revolve around a projection object to take one or more projection images. Radiation source 201 (or a radiation sub-source) may revolve around a projection object in any angle range (e.g., −15° to +15°, −25° to +25°, −40° to +65°, −65° to +90°, etc.) when the vertical direction is denoted as 0°, a negative angle indicates an anti-clockwise rotation, and a positive angle indicates a clockwise rotation. Radiation source 201 (or a radiation sub-source) may emit radiation at any fixed frequency of angle (e.g., in every 1°, in every 2°, in every 5°, and in every 10°, etc.). For example, radiation source 201 (or a radiation sub-source) may emit radiation at a fixed frequency of every 5° with an angle range −15° to +15° (i.e., at −15°, −10°, −5°, 0°, +5°, +10°, +15°). Radiation source 201 (or a radiation sub-source) may emit radiation at a variable frequency of angle. For example, radiation source 201 (or a radiation sub-source) may emit radiation in 1°, 4°, 10°, 30°, and 90°.

Merely by way of example, radiation source 201 (or a radiation sub-source) may revolve around a projection object between −15° to +15° and emit radiation at every 1°. In that case, 31 projection images may be generated. As another example, radiation source 201 (or a radiation sub-source) may revolve around projection object between −25° to +25° and emit radiation at every 2°. In that case, 26 projection images may be generated.

Compression plate 202 and detector 203 and may hold the projection object from two opposite (or essentially opposite) directions. Compression plate 202 may be made of a rigid material. Compression plate 202 may be flat or curved. In some embodiments, compression plate 202 may be made of a material transparent to radiation (e.g., X-ray, etc.). Compression plate 202 may be parallel (or essentially parallel) to detector 203 (shown in FIG. 2A).

Detector 203 may measure the flux, spatial distribution, spectrum, and/or other properties of radiations. Radiation emitted by radiation source 201 may pass through a projection object and reach detector 203 to generate a projection image on detector 203. Detector 203 may be a direct semiconductor detector, a gas-filled detector, a scintillation detector, or the like, or a combination thereof. Detector 203 may have an energy resolution including, for example, 125 eV, 145 eV, 165 eV, 180 eV, 190 eV, 205 eV, 225 eV, etc. Detector 203 may have a detecting area of, for example, 6 mm$^2$, 7 mm$^2$, 13 mm$^2$, 25 mm$^2$, etc. Detector 203 may have a thickness of, for example, 200 µm, 300 µm, 450 µm, 500 µm, 700 µm, etc. Detector 203 may have a peaking time of, for example, 11.2 µs, 32 µs, 44.8 µs, etc.

In some embodiments, a projection object may be a mammary gland. A projection image may be a projection image of the mammary gland. Radiation source 201 may be an X-ray source. Detector 203 may be an X-ray detector.

A projection image taken by imaging device 110 may be sent to image processing device 120, data base 150, display 140, and/or terminal 130 via network 160 shown in FIG. 1. In some embodiments, the projection image taken by imaging device 110 may be sent to image processing device 120. Image processing device 120 may process the projection image. For example, image processing device 120 may generate a 3D reconstructed image based on a plurality of projection images. In some embodiments, the projection image may be a projection image of a mammary gland. Image processing device 120 may generate a 3D reconstructed image of a mammary gland based on a plurality of projection images of the mammary gland. The 3D mammary gland reconstructed image may include one or more tomographic images of a mammary gland.

It should be noted that the descriptions above in relation to imaging device 110 is provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure.

Figure 2B:
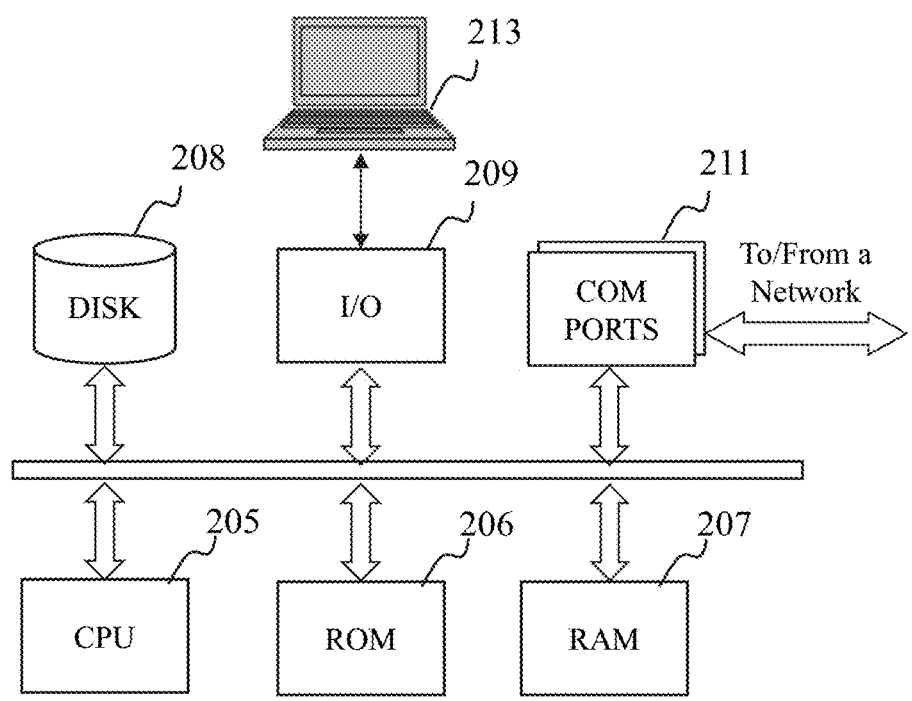
FIG. 2B illustrates an architecture of a computer which may be used to implement a specialized system incorporating the present teaching.

FIG. 2B illustrates an architecture of a computer 200 which may be used to implement a specialized system incorporating the present teaching. Such a specialized system incorporating the present teaching has a functional block diagram illustration of a hardware platform that includes user interface elements. Computer 200 may be a general purpose computer or a special purpose computer. Both may be used to implement a specialized system for the present teaching. Computer 200 may be used to implement any component of image processing as described herein. For example, image processing device 120, etc. may be implemented on a computer such as computer 200, via its hardware, software program, firmware, or a combination thereof. Although only one such computer is shown, for convenience, the computer functions relating to image processing as described herein may be implemented in a distributed fashion on a number of similar platforms, to distribute the processing load. In some embodiments, computer 200 may be used as imaging processing device 120 shown in FIG. 1.

Computer 200, for example, may include COM ports 211 connected to and from a network connected thereto to facilitate data communications. Computer 200 may also include a central processing unit (CPU) 205, in the form of one or more processors, for executing program instructions. The exemplary computer platform may include an internal communication bus 204, program storage, and data storage of different forms, e.g., disk 208, read only memory (ROM) 206, or random access memory (RAM) 207, for various data files to be processed and/or communicated by the computer, as well as possibly program instructions to be executed by CPU 205. Computer 200 may also include an I/O component 209, supporting input/output flows between the computer and other components therein such as user interface elements 213. Computer 200 may also receive programming and data via network communications.

Hence, aspects of the methods of the image processing and/or other processes, as described herein, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors, or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of a scheduling system into the hardware platform(s) of a computing environment or other system implementing a computing environment or similar functionalities in connection with image processing. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s), or the like, which may be used to implement the system or any of its components shown in the drawings. Volatile storage media may include dynamic memory, such as a main memory of such a computer platform. Tangible transmission media may include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media may include, for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described herein may be embodied in a hardware device, it may also be implemented as a software only solution—e.g., an installation on an existing server. In addition, image processing as disclosed herein may be implemented as a firmware, firmware/software combination, firmware/hardware combination, or a hardware/firmware/software combination.

Figure 3A:
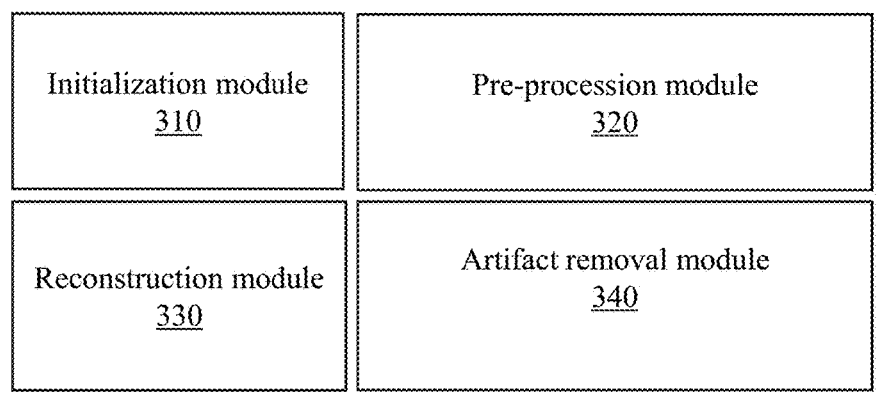
FIG. 3A illustrates an exemplary image processing device according to some embodiments of the present disclosure.

FIG. 3A illustrates an exemplary image processing device 120 according to some embodiments of the present disclosure. Image processing device 120 may include an initialization module 310, a pre-processing module 320, a reconstruction module 330, and an artifact removal module 340. Components in image processing device 120 may be connected to or communicate with each other and other components in image reconstruction system 100, for example, imaging device 110, terminal 130, display 140, database 150, or the like, or a combination thereof.

Initialization module 310 may initialize or adjust one or more parameters relating to the configuration of image reconstruction system 100. For example, the parameter(s) may be related to imaging device 110, image processing device 120, and terminal 130, or the like, or a combination thereof. The parameter(s) may be obtained from imaging device 110, image processing device 120, terminal 130, database 150, or the like, or a combination thereof. The parameter(s) may be determined based on data obtained from imaging device 110, image processing device 120, terminal 130, database 150, or the like, or a combination thereof.

The parameter(s) may include a coordinate of the radiation source, a radiation angle of the radiation source, the coordinate of a rotating center of the radiation source, the pixel size of a projection image, the width of a projection image, the height of a projection image, the coordinate vector of a pixel in a projection image, or the like, or a combination thereof.

In some embodiments, the parameter(s) may be a physical coordinate of image reconstruction system 100 (e.g., the coordinate of the radiation source, a radiation angle of the radiation source, and the coordinate of a rotating center of the radiation source, etc.), and an image parameter of a projection image (e.g., the pixel size of a projection image, the width of a projection image, and the height of a projection image, etc.).

Pre-procession module 320 may pre-process images. The images may be obtained by imaging device 110 or retrieved from another source (e.g., a database 150, a storage, etc.). Pre-procession module 320 may perform one or more pre-processing operations on the image. The pre-processing operations may include, for example, image segmentation, image negative film generation, geometrical error removal, color correction, geometric transformation, image noise reduction, image enhancement, image compression, or the like, or a combination thereof.

Figure 3B:
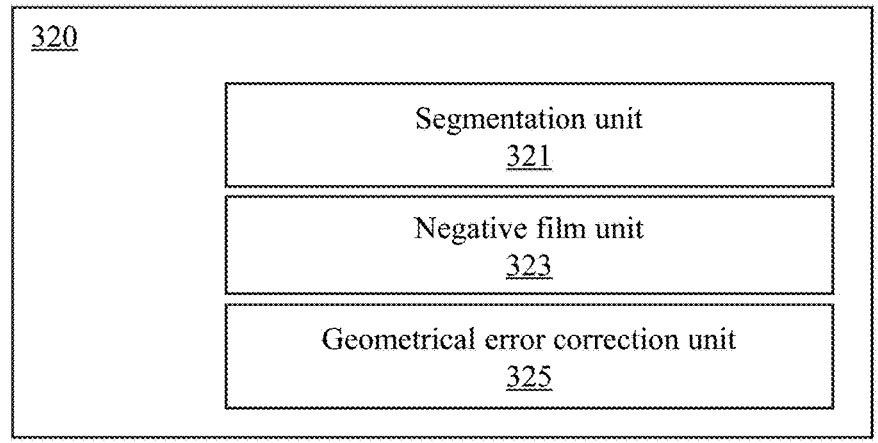
FIG. 3B is a block diagram illustrating an exemplary pre-procession module according to some embodiments of the present disclosure.

As illustrated in FIG. 3B, pre-procession module 320 may include a segmentation unit 321, a negative film unit 323, and a geometrical error correction unit 325. Segmentation unit 321 may segment a projection image to generate a segmented projection image. Negative film unit 323 may generate a negative film of an image (e.g., a segmented projection image, etc.). Geometrical error correction unit 325 may correct a geometrical error of an image (e.g., a negative film of a segmented projection image, etc.).

Image segmentation may be performed based on, for example, an edge detecting method, a threshold segmenting method, a histogram-based method, a clustering method, a compression-based method, a region-growing method, a graph partitioning method, or the like, or a combination thereof. The image segmentation operation may be performed by segmentation unit 321. In some embodiments, image segmentation may be performed based on a region-growing method that may also be referred as a seed filling method. More descriptions about seed filling method may be found elsewhere in the present disclosure. See, for example, FIG. 6 and FIG. 7, and the description thereof.

In some embodiments, a projection image may be a projection image of a mammary gland (or referred to as a mammary gland projection image). The mammary gland projection image may be pre-processed by one or more pre-processing operations including, for example, image segmentation, image negative film generation, geometrical error removal, or the like, or a combination thereof.

Pre-procession module 320 may generate a processed image. The processed image may be sent to one or more other components in image processing device 120, for example, reconstruction module 330, artifact removal module 340, or the like, or a combination thereof. The processed image may be sent to one or more components in reconstruction system 100, for example, terminal 130, display 140, database 150, or the like, or a combination thereof.

In some embodiments, pre-procession module 320 may pre-process a mammary gland projection image. The projection image may be obtained by imaging device 110 or retrieved from another source (e.g., a database 150, a storage, etc.). Pre-procession module 320 may generate a processed mammary gland projection image. The processed mammary gland projection image may be send to, for example, reconstruction module 330, artifact removal module 340, or the like, or a combination thereof.

Reconstruction module 330 may perform image reconstruct. The image(s) subject to the reconstruction may be a projection image (e.g., a mammary gland projection image, etc.) or a processed projection image (e.g., a processed mammary gland projection image, etc.), or the like, or a combination thereof. The projection image may be generated by imaging device 110 or retrieved from another source (e.g., database 150, and a storage, etc.). The processed projection image may be generated by pre-procession module 320 or retrieved from another source (e.g., database 150, and a storage, etc.). In some embodiments, the projection image may be generated by imaging device 110, and the processed image may be generated by pre-procession module 320. In some embodiments, the projection image may be a mammary gland projection image obtained by image device 110 and a processed image may be a processed mammary gland image generated by pre-procession module 320.

Figure 3C:
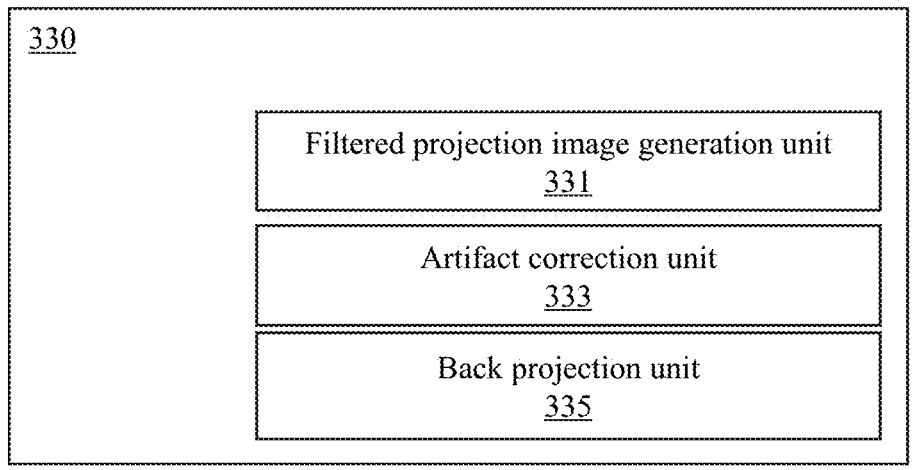
FIG. 3C is a block diagram illustrating an exemplary reconstruction module according to some embodiments of the present disclosure.

As illustrated in FIG. 3C, the reconstruction module 330 may include a filtered a projection image generation unit 331, an artifact correction unit 333, and a back projection unit 335. Filtered a projection image generation unit 331 may generate a filtered projection image including a highlighted artifact and an X-ray attenuation artifact. Artifact correction unit 333 may correct the highlighted artifact and the X-ray attenuation artifact in the filtered projection image to generate a first image. Back projection unit 335 may perform back projection to generate the reconstructed image based on the first image.

Reconstruction module 330 may generate a reconstructed image based on acquired images. The reconstructed image may include one or more tomographic images. The reconstructed image may be a 3D image. In some embodiments, the reconstructed image may be a 3D tomographic mammary gland reconstructed image. The reconstructed image generated by reconstruction module 330 may be sent to other component(s) in image processing device 120, for example, pre-procession module 320, artifact removal module 340, or the like, or a combination thereof. The reconstructed image may be sent to one or more components in reconstruction system 100, for example, terminal 130, display 140, database 150, or the like, or a combination thereof.

Reconstruction module 330 may perform image reconstruction based on an image reconstruction method. The image reconstruction method may include filtered back projection (FBP), a simultaneous iterative reconstruction technique (SIRT), matrix inversion tomosynthesis (MITS), iterative maximum a posteriori statistical reconstruction, a Bayesian-based interactive reconstruction method, or the like, or a combination thereof. In some embodiments, reconstruction module 330 may reconstruct a mammary gland reconstructed image utilizing a filtered back projection method. More descriptions regarding filtered back projection may be found elsewhere in the present disclosure. See, for example, FIG. 4 and FIG. 8, and the description thereof.

Figure 3D:
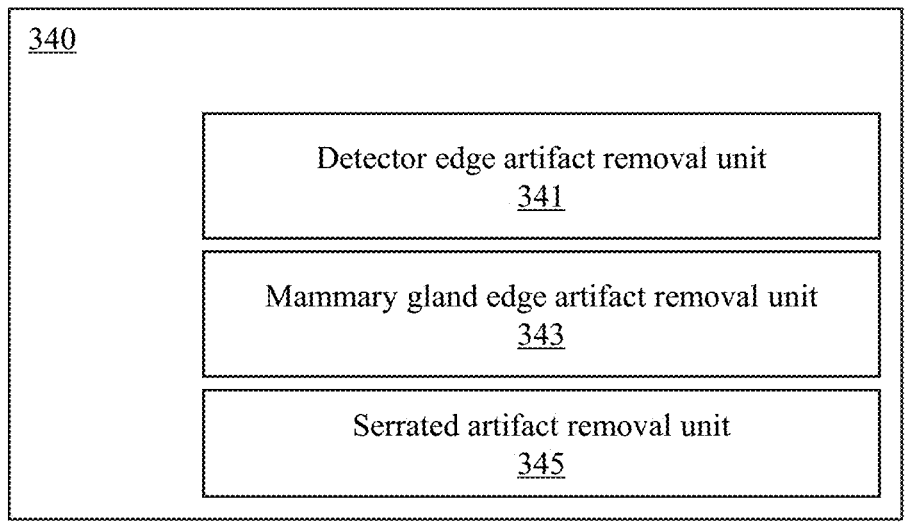
FIG. 3D is a block diagram illustrating an exemplary artifact removal module according to some embodiments of the present disclosure.

As illustrated in FIG. 3D, artifact removal module 340 may include a detector edge artifact removal unit 341, a mammary gland edge artifact removal unit 343, and a serrated artifact removal unit 345. Detector edge artifact removal unit 341, mammary gland edge artifact removal unit 343, and serrated artifact removal unit 345 may be connected to or communicated with each other. Artifact removal module 340 may be connected to or communicated with other component(s) in image processing device 120, for example, initialization module 310, pre-precession module 320, or reconstruction module 330, or the like, or a combination thereof. Artifact removal module 340 may be connected to or communicated with unit in reconstruction system 100, for example, terminal 130, display 140, database 150, or the like, or a combination thereof.

Artifact removal module 340 may remove artifact in a reconstructed image. The reconstructed image may be generated by reconstruction module 330 or retrieved from another source (e.g., database 150, and a storage, etc.). The reconstructed image may include one or more tomographic images that may depict one or more layers of a projection object. In some embodiments, the reconstructed image may be a mammary gland reconstructed image.

Artifact may be any error in a perception or representation in a reconstructed image. Artifact may include detector edge artifact, mammary gland edge artifact, artifact caused by the movement of a patient, metal artifact, artifact caused by the arcing of a radiation source (e.g., a bulb, etc.), artifact caused by a deviation of a detector from its normal operation condition, or the like, or a combination thereof. An artifact may have a regular shape (for example, streaking, ring, serration, etc.), or an irregular, or the like, or a combination thereof. In some embodiments, artifacts may include detector edge artifact, mammary gland edge artifact, serrated artifact, or the like, or a combination thereof.

Artifact removal module 340 may remove artifact utilizing various artifact removing methods. The artifact removing method may include a polynomial interpolation method, an iterative deblurring method, an expectation-maximization method, an algebraic reconstruction technique, a Markov random field method, a wavelet method, an ordered subsets convex iterative method, a beam-stop technique, a scanning lead-strip technique, or the like, or a combination thereof.

Detector edge artifact removal unit 341 may remove detector edge artifact. Detector edge artifact may have a strip shape, as shown in area 1210 in FIG. 12. Detector edge artifact may be caused by a dark current, a gain, a nonlinear error, a radiation damage, response nonuniformity, detector afterglow, or the like, or a combination thereof. Detector edge artifact may be removed by setting a gray value in an area of detector edge artifact based on the gray value of pixels in a neighborhood of the detector edge artifact. More descriptions regarding removing detector edge artifact may be found elsewhere in the present disclosure. See, for example, FIG. 9 and the description thereof.

Figure 14:
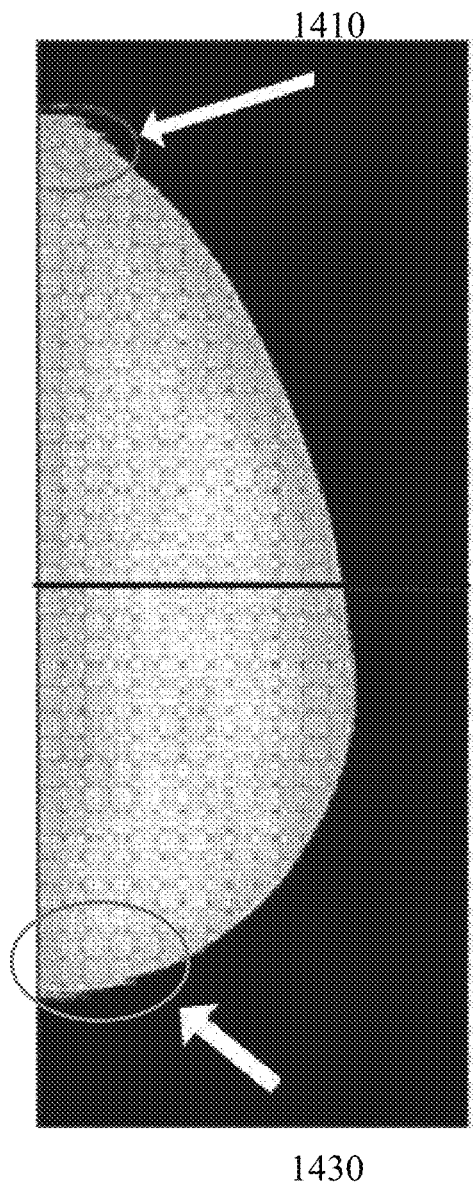
FIG. 14 illustrates an exemplary reconstructed image of a mammary gland without serrated artifact correction.

A mammary gland tomographic image whose detector edge artifact have been removed by detector edge artifact removal unit 341 may still include a serrated artifact, as shown in area 1410 in FIG. 14. The serrated artifact may be removed by serrated artifact removal unit 345. In some embodiments, serrated artifact may be removed based on an intersection point corresponding to a detector edge and a mammary gland edge, and corresponding dislocation information. More descriptions regarding removing serrated artifact may be found elsewhere in the present disclosure. See, for example, FIG. 10 and FIG. 11, and the description thereof.

Figure 21:
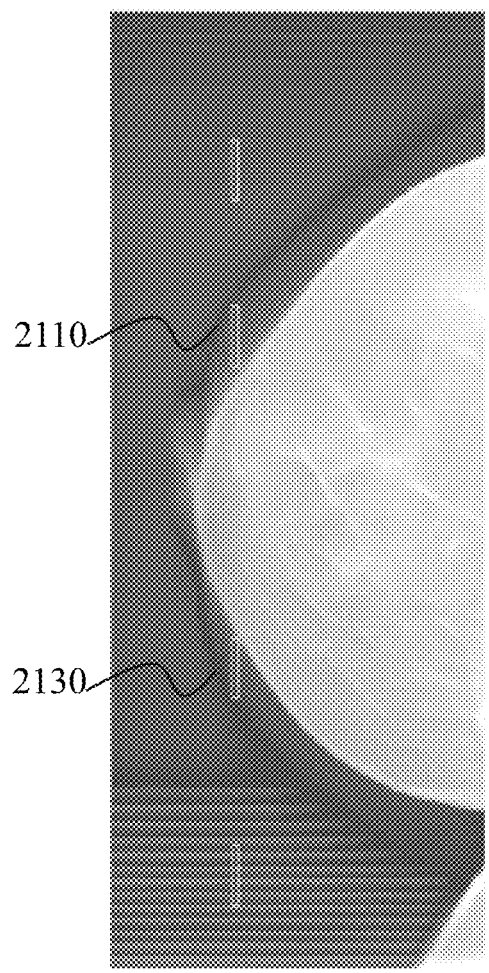
FIG. 21 illustrates an exemplary reconstructed image of a mammary gland.

Mammary gland edge artifact removal unit 343 may remove mammary gland edge artifact. FIG. 21 illustrates a mammary gland reconstructed image. As shown in FIG. 21, there are mammary gland edge artifact in area 2110 and area 2130. More descriptions regarding removing mammary gland edge artifact may be found elsewhere in the present disclosure. See, for example, FIG. 9 and the description thereof.

It should be noted that the descriptions above in relation to image processing device 120 is provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. For example, reconstruction module 330 may include a filtered back projection unit (no shown in figures) that may perform filtered back projection of a mammary gland projection image. As another example, artifact removal module 340 may include one or more additional artifact removal units (no shown in figures) that may remove one or more other kinds of artifact (e.g., artifact caused by the movement of a patient, metal worn by a patient when the patient is scanned, the arcing of a bulb, and the deviation of a detector from its normal operation condition, etc.). In some embodiments, the projection object may be an organism, and an organ (e.g., a mammary gland, a hand, a head, a lung, etc.), or the like, or a combination thereof.

Figure 4:
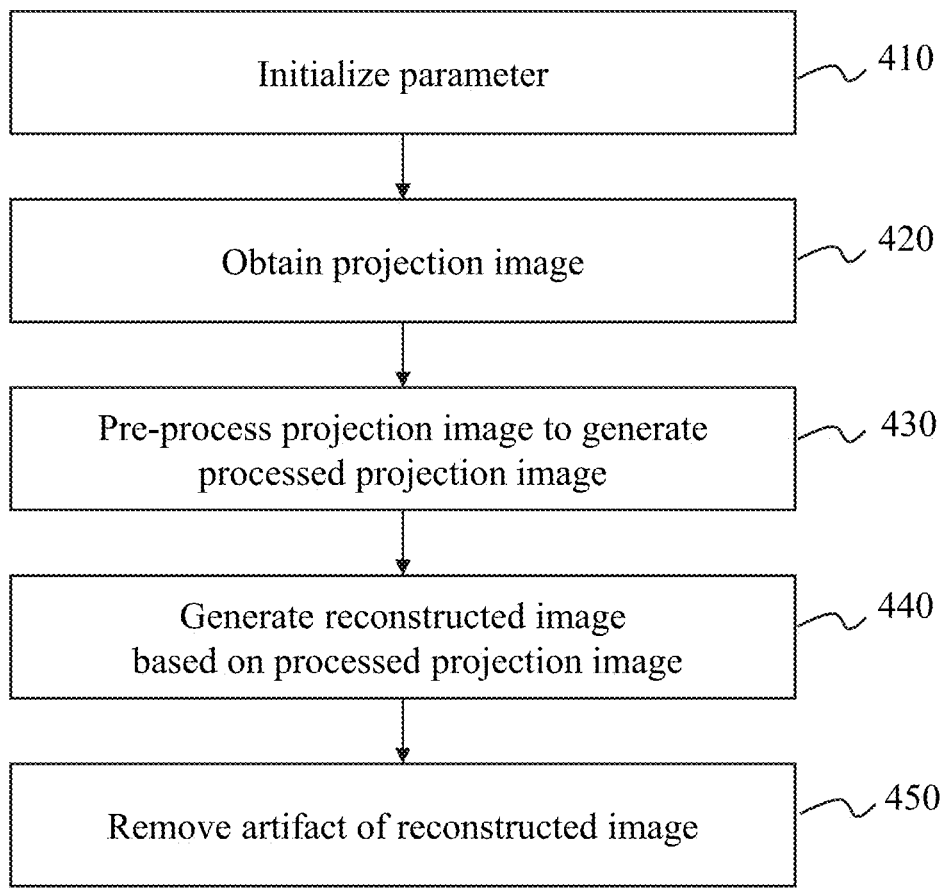
FIG. 4 illustrates a flowchart illustrating an exemplary process for image reconstruction in accordance with some embodiments of the present disclosure.

FIG. 4 illustrates a flowchart illustrating an exemplary process 400 for image reconstruction in accordance with some embodiments of the present disclosure. In some embodiments, process 400 may be performed by one or more devices (e.g., image processing device 120) in image reconstruction system 100 (shown in FIG. 1) and image processing device 120 (shown in FIG. 3A). In some embodiments, at least part of process 400 may be performed by computer 200 shown in FIG. 2B.

In 410, one or more parameters may be initialized or adjusted. The parameter initialization or adjustment in 410 may be performed by initialization module 310 of FIG. 3A. The parameters may be related to the configuration of image reconstruction system 100. For example, the parameters may be related to imaging device 110, image processing device 120, and terminal 130, or the like, or a combination thereof.

The parameters may be obtained from imaging device 110, image processing device 120, terminal 130, database 150, or the like, or a combination thereof. The parameters may be determined based on data obtained from, for example, imaging device 110, image processing device 120, terminal 130, database 150, or the like, or a combination thereof. Detailed descriptions about the parameters may be found elsewhere in the present disclosure. See, for example, FIG. 3A and the description thereof. In some embodiments, the parameters may be a physical coordinate of image reconstruction system 100 and an image parameter of a projection image.

In 420, one or more projection images may be obtained. The projection image(s) may be obtained by imaging device 110 or retrieved from another source (e.g., database 150, a storage, etc.). In some embodiments, the projection image may be a mammary gland projection image.

In 430, the projection image may be a processed projection image that has been subject to one or more pre-processing operations. Pre-processing in 430 may be performed by pre-procession module 320 illustrated in FIG. 3A. A projection image may be pre-processed utilizing a pre-processing method including, for example, image segmentation, image negative film generation, geometrical error removal, color correction, geometric transformation, image noise reduction, image enhancement, image compression, the like, or a combination thereof. In some embodiments, a projection image may be a mammary gland projection image. More descriptions regarding methods of pre-processing a projection image may be found elsewhere in the present disclosure. See, for example, FIG. 5 and the description thereof.

In 440, the processed projection image may be reconstructed to generate a reconstructed image. Image reconstruction in 440 may be performed by reconstruction module 330 of FIG. 3A. The reconstructed image may include one or more tomographic images that may depict one or more layers of a projection object. The processed projection image may be reconstructed utilizing a reconstruction method. Exemplary reconstruction method may include filtered back projection, a simultaneous iterative reconstruction technique (SIRT), matrix inversion tomosynthesis (MITS), iterative maximum a posteriori statistical reconstruction, a Bayesian-based interactive reconstruction method, or the like, or a combination thereof.

Merely by way of example, a processed projection image may be a processed mammary gland projection image, and a reconstructed image may be a mammary gland reconstructed image. The processed mammary gland projection image may be reconstructed utilizing filtered back projection. More descriptions regarding back projection reconstruction method may be found elsewhere in the present disclosure. See, for example, FIG. 8 and the description thereof.

In 450, artifact in the reconstructed image may be removed. Artifact removal in 450 may be performed by artifact removal module 340 of FIG. 3A. The artifact may be take the form of any shape and/or type. More descriptions regarding artifact may be found elsewhere in the present disclosure. See, for example, FIG. 3A and the description thereof.

Artifact in a reconstructed image may be removed utilizing an artifact removing method. The artifact removing method may include a polynomial interpolation method, an iterative deblurring method, an expectation-maximization method, an algebraic reconstruction technique, a Markov random field method, a wavelet method, an ordered subsets convex iterative method, a beam-stop technique, a scanning lead-strip technique, or the like, or a combination thereof.

In some embodiments, a reconstructed image may be a mammary gland reconstructed image. Artifact in a reconstructed image may include detector edge artifact, mammary gland edge artifact, serrated artifact, or the like, or a combination thereof. More descriptions regarding artifact removing method may be found elsewhere in the present disclosure. See, for example, FIG. 9 and the description thereof.

It should be noted that process 400 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protection scope of the present disclosure. In some embodiments, some steps may be reduced or added. For example, 430 may be omitted. A reconstructed image may be generated based on an original projection image without pre-processing. As another example, 450 may be omitted. In some embodiments, the projection object may be an organism, an organ (e.g., a mammary gland, a hand, a head, a lung, etc.), or the like, or a combination thereof. Similar modifications should fall within the scope of the present disclosure.

Figure 5:
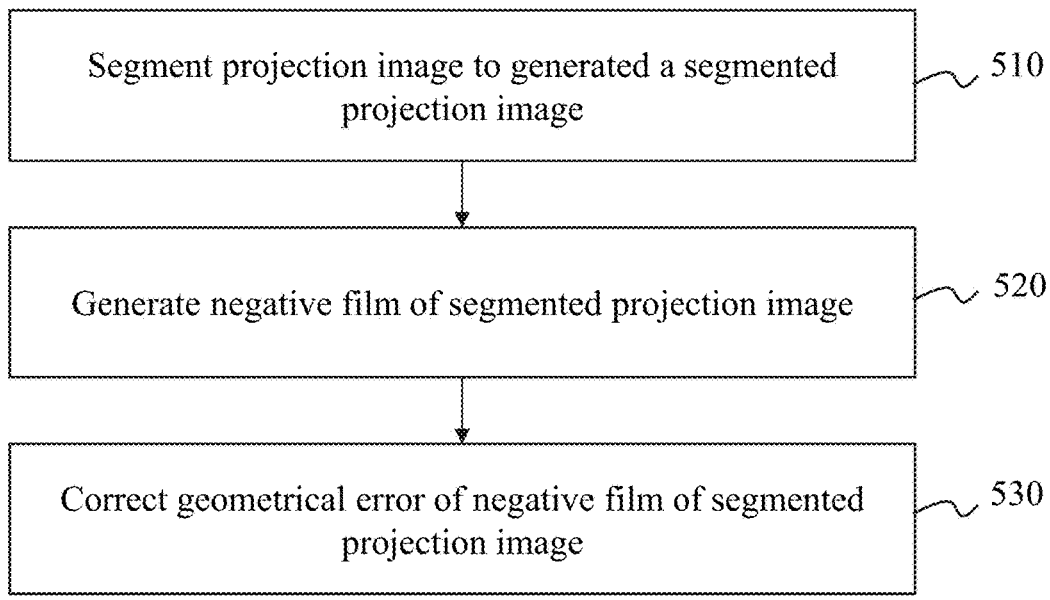
FIG. 5 is a flowchart illustrating an exemplary process for pre-processing projection image in accordance with some embodiments of the present disclosure.

FIG. 5 is a flowchart illustrating an exemplary process 500 for pre-processing projection image in accordance with some embodiments of the present disclosure. In some embodiments, process 500 may be performed by pre-processing module 320 in imaging processing device 120 (shown in FIG. 3A and FIG. 3B). In some embodiments, process 500 described with reference to FIG. 5 may be an exemplary process for achieving 430 shown in FIG. 4.

In 510, a projection image may be segmented to obtain a segmented projection image including a region of interest. Image segmentation in 510 may be performed by segmentation unit 321 of FIG. 3B. The projection image may be obtained by imaging device 110 or retrieved from another source (e.g., a database 150, a storage, etc.). The projection image may be segmented utilizing an image segmentation method. The image segmentation method may include an edge detecting method, a threshold segmenting method, a histogram-based method, a clustering method, a compression-based method, a region-growing method, a graph partitioning method, or the like, or a combination thereof.

An edge detection method may be performed based on an edge detection algorithm. The edge detection algorithm may include, for example, the Sobel edge detection algorithm, the Canny edge detection algorithm, a phase congruency-based algorithm, or the like, or a combination thereof.

A threshold segmenting method may be performed by classifying pixels in an image based on a fixed pixel value. For example, a pixel may be deemed as a black pixel if its pixel value exceeds the fixed pixel value; a pixel may be deemed a white pixel if its pixel value is smaller than the fixed pixel value.

A region-growing method may also be referred as a seed filling method. A region-growing method may be performed by selecting one or more seeds and determining whether one or more neighboring pixels of the selected seeds may be added to the region.

A histogram-based method may be performed by determining a gray value histogram based on the gray value of pixels in an image. One or more peaks and valleys in a histogram may be used to determine an edge of a region of interest in the image.

In some embodiments, a projection image may be a mammary gland projection image. The mammary gland projection image may be segmented to obtain a region of mammary gland. The mammary gland projection image may be segmented utilizing the region-growing method that may be also be referred to as the seed filling method. More descriptions regarding region-growing method may be found elsewhere in the present disclosure. See, for example, FIG. 7 and the description thereof.

In 520, a segmented projection image may be processed to generate a negative film. Negative film operation in 520 may be performed by negative film unit 323 of FIG. 3B. A negative film may be an image in which the darkness of a portion of the projection object reversely relates to the darkness of the same portion in the film or image. For instance, in a negative film, a lightest area of the projection object appears darkest in the film, and a darkest area of the projection object appears lightest in the film.

In some embodiments, 520 may include one or more of the following operations. A maximum gray value Max_A in a segmented projection image may be determined. A corrected gray value of each pixel in the segmented projection image may be determined by subtracting its gray value from Max_A. The corrected gray value of a pixel may be assigned to the pixel as its gray value.

In 530, a geometrical error of the negative film of a segmented projection image may be corrected. Geometrical error correction operation in 530 may be performed by geometrical error correction unit 325 of FIG. 3B. A geometrical error may include, for example, a translation error of the detector, a rotation error of the detector, or the like, or a combination thereof.

A translation error of the detector may be caused by the translation of the detector in a horizontal direction. As used herein, "horizontal direction" may refer to a direction along the x-y plane shown in FIG. 2A. In some embodiments, the translation error of the detector may be removed by one or more of the following operations. A coordinate matrix of the pixels in a segmented projection image in a first coordinate system may be obtained. A translation vector of a pixel in the first coordinate system and in a second coordinate system may be determined. In some embodiments, the translation vector may be determined by subtracting the coordinate of a pixel in the first coordinate system from its coordinate in the second coordinate system. A corrected coordinate matrix of pixels of the segmented projection image in the second coordinate system may be determined based on the coordinate matrix of the first coordinate system and the translation vector.

A rotation error of the detector may be caused by a rotation of the detector about a vertical direction. As used herein, "vertical direction" may refer to a direction along the z-axis shown in FIG. 2A. In some embodiments, a rotation error of the detector may be removed by one or more of the following operations. A mapping relationship between a coordinate matrix of pixels in a segmented projection image in a first coordinate system and its coordinate system in a second coordinate system may be determined. A coordinate of each pixel in the second coordinate system may be determined based on the mapping relationship. A gray value of each pixel in the segmented projection image may be determined by utilizing an interpolation algorithm. The interpolation algorithm may include an image interpolation algorithm, a bilinear interpolation algorithm, a recent field interpolation algorithm, or the like, or a combination thereof.

It should be noted that process 500 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. In some embodiments, some steps may be reduced or added. For example, 520 may be omitted. As another example, 530 may be omitted. In some embodiments, 510, 520, and 530 may be performed in any order. For example, 520 may be performed before 510. A projection image may be processed to generate a negative film first and then be segmented. As a further example, 530 may be performed before 510 and 520. Similar modifications should fall within the scope of the present disclosure.

Figure 6:
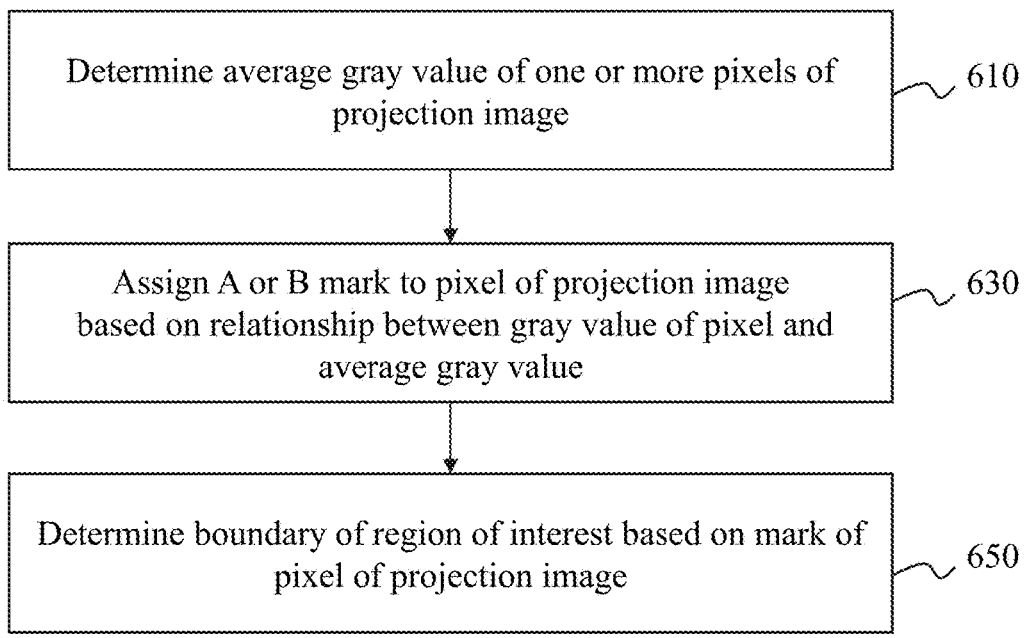
FIG. 6 is a flowchart illustrating an exemplary process for segmenting projection image in accordance with some embodiments of the present disclosure.

FIG. 6 is a flowchart illustrating an exemplary process 600 for segmenting a projection image in accordance with some embodiments of the present disclosure. In some embodiments, process 600 may be performed by pre-procession module 320 in imaging processing device 120 (shown in FIG. 3A). In some embodiments, process 600 described with reference to FIG. 6 may be an exemplary process for achieving 510 shown in FIG. 5.

In 610, an average gray value of one or more pixels of a projection image may be determined. The projection image may be obtained by imaging device 110 or retrieved from another source (e.g., a database 150, a storage, etc.). In some embodiments, the projection image may be a mammary gland projection image.

In 630, one of two marks, e.g., mark A or mark B, may be assigned to one or more pixels of the projection image based on the relationship between the gray value of a pixel and the average gray value. Merely by way of example, mark A may correspond to the value of 0, and mark B may correspond to the value of 1.

The relationship between the gray value of a pixel and the average gray value may be determined according to any rule. In some embodiments, the relationship may be determined according numerical values of the gray value of a pixel and the average gray value. For example, A may be assigned to a pixel when its gray value is less than the average gray value. B may be assigned to a pixel when its gray value is not less than average gray value. As another example, A may be assigned to a pixel when the difference between its gray value and the average gray value is not less than a first number, for example, 1, or 5, or 10, or the like. B may be assigned to a pixel when the difference between its gray value and the average gray value is less than a second number, for example, 1, or 4, or 7, and the like. The first number may be the same as or different from the second number.

In 650, the boundary of a region of interest may be determined based on the marks of pixels in the projection image. A region of interest may also be referred to as a target area. In some embodiments, a region of interest may be a region of a mammary gland in a projection image. The boundary of the region of interest may be determined utilizing an edge detecting method, a threshold segmenting method, a histogram-based method, a clustering method, a compression-based method, a region-growing method, a graph partitioning method, or the like, or a combination thereof. More descriptions regarding region-growing method may be found elsewhere in the present disclosure. See, for example, FIG. 7 and the description thereof.

In some embodiments, a segmented projection image may include a region of interest determined by process 600. In some embodiments, a segmented projection image may include a segmented region based on a plurality of regions of interest. The plurality of regions of interest may be determined by process 600, respectively, based on a plurality of projection images.

Figure 19:
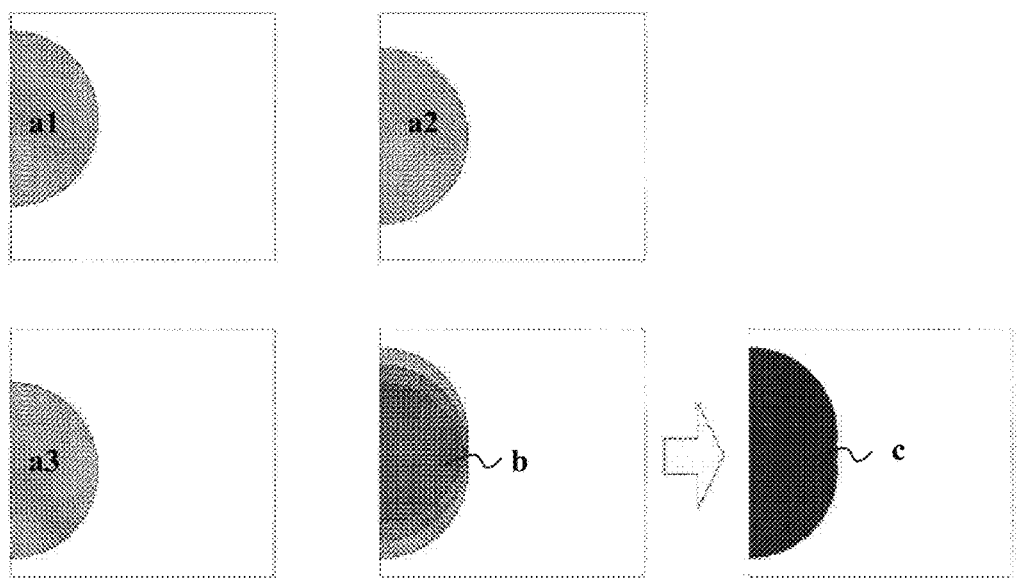
FIG. 19 illustrates a process for generating a segmented region by merging a plurality of regions of interest according to some embodiments of the present disclosure.
Figure 20:
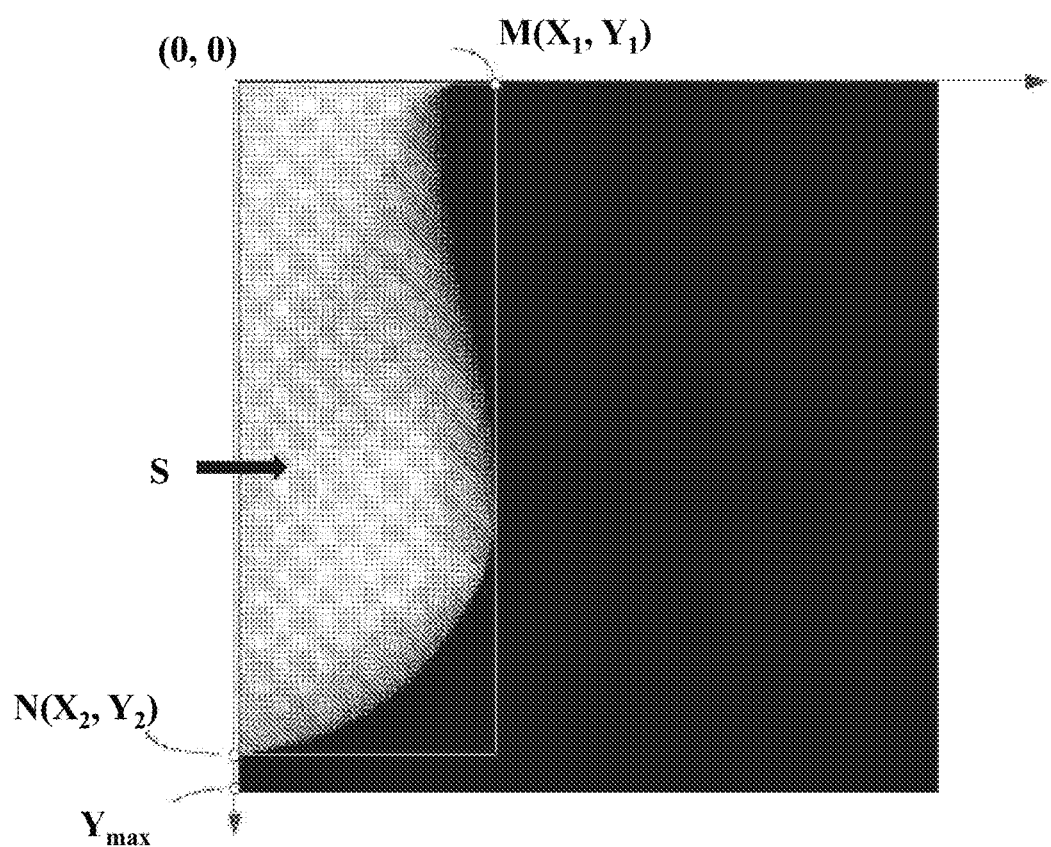
FIG. 20 illustrates a process for generating a segmented region based on a rectangular segmenting algorithm according to some embodiments of the present disclosure.

A segmented region may be determined by various ways. In some embodiments, the segmented region may be a union of a plurality of regions of interest. As shown in FIG. 19, a1, a2, and a3 illustrate three regions of interest, and b illustrates the overlapping of a1, a2, and a3. A segmented region is region c, which is a union of a1, a2, and a3. In some embodiments, the segmented region may be determined based on the coordinates of pixels in regions of interest. As shown in FIG. 20, the segmented region may be rectangle S whose diagonal vertexes may be $M(X_1, Y_1)$ and $N(X_2, Y_2)$. $X_1$ may be the largest horizontal coordinate value of all pixels of the plurality of regions of interest. $Y_1$ may be the smallest longitudinal coordinate value of all pixels of the plurality of regions of interest. $X_2$ may be the smallest horizontal coordinate value of all pixels of the plurality of regions of interest. $Y_2$ may be the largest longitudinal coordinate value of all pixels of the plurality of regions of interest. In some embodiments, $X_2$ may be 0 if the projection image is taken when a patient is standing. In some embodiments, $Y_1$ may be 0 if the projection image is taken when the patient is lying. In some embodiments, $X_1$ may be the largest horizontal coordinate value of all pixels of the plurality of regions of interest. $Y_1$ and $X_2$ may be 0. $Y_2$ may be the largest height of the plurality of projection images.

It should be noted that process 600 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. In some embodiments, in 610, the median value or mode or any other statistic of the gray values of one or more pixels of a projection image may be determined based on the gray value of the one or more pixels of the projection image. In 630, a mark may be assigned to a pixel of a projection image based on the relationship between the gray value of the pixel and the median value or mode or any other statistic parameter of the gray values of one or more pixels of a projection image. In some embodiments, in 630, any number of marks may be assigned to a pixel of a projection image based on the relationship between the gray value of a pixel and the average gray value. For example, the number of marks that may be assigned to a pixel may be three, four, five, or the like, or a combination thereof. Similar modifications should fall within the scope of the present disclosure.

Figure 7:
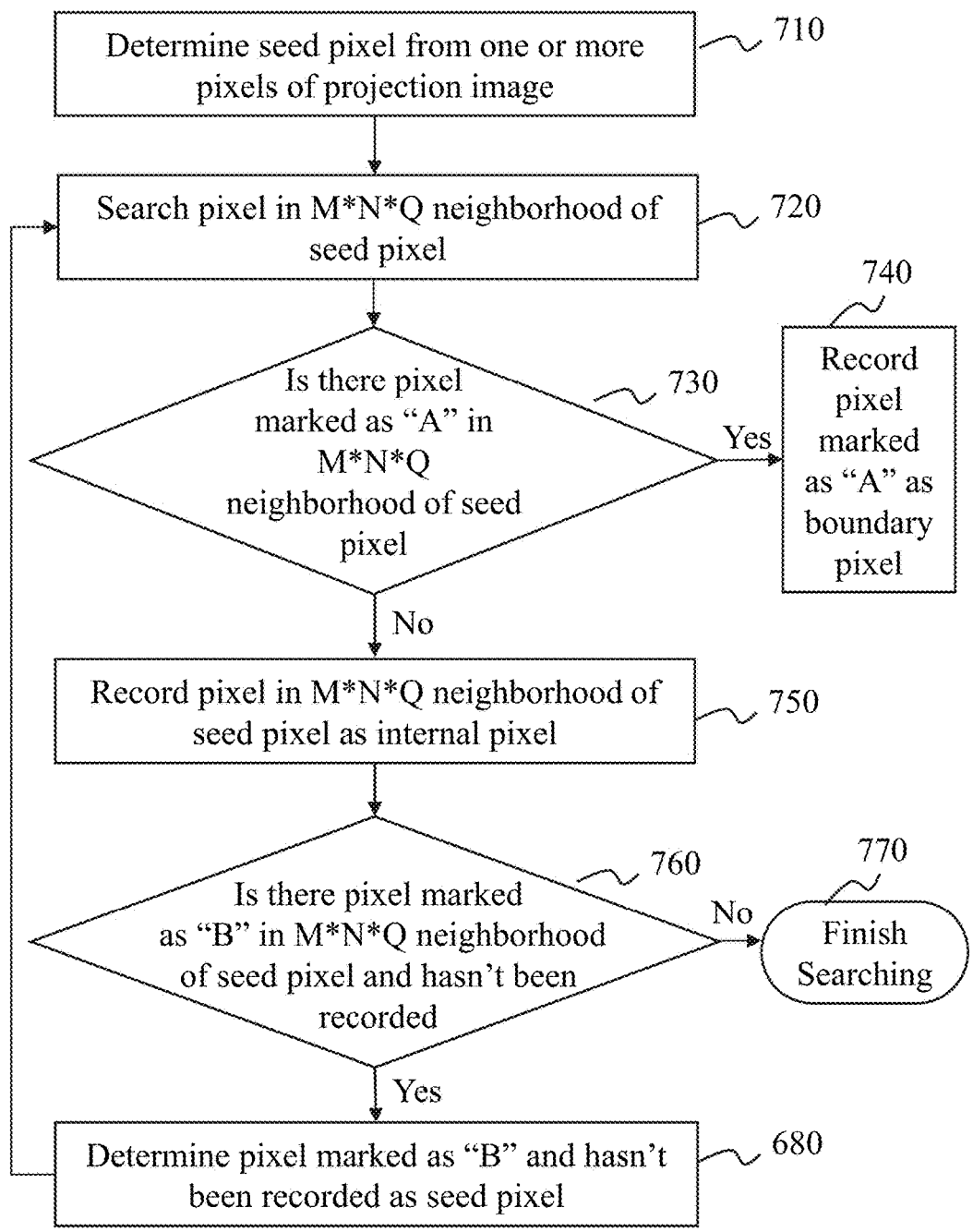
FIG. 7 is a flowchart illustrating an exemplary process for determining the boundary of a region of interest in accordance with some embodiments of the present disclosure.

FIG. 7 is a flowchart illustrating an exemplary process 700 for determining the boundary of a region of interest in accordance with some embodiments of the present disclosure. Process 700 may also be referred to as a region-growing method or a seed filling method. In some embodiments, process 700 may be performed by pre-procession module 320 in imaging processing device 120. In some embodiments, process 700 described with reference to FIG. 7 is an exemplary process for achieving 650 shown in FIG. 6.

In 710, a seed pixel, or referred to as a seed, may be determined from one or more pixels of a projection image. The seed pixel may be any pixel in the projection image. In some embodiments, the seed pixel may be a pixel whose gray value is not less than the average gray value, which may be assigned mark B according to the example described above. In some embodiments, the seed pixel may be a pixel in the lower left corner or the upper left corner of a projection image and whose mark is B.

In 720, pixels in a M×N×Q neighborhood of the seed pixel may be searched. M, N, and Q may be a positive integer of any value. At least two of M, N, and Q may be equal to each other, or different from each other. In some embodiments, M, N, and P may equal to 3. Some or all pixels in the M×N×Q neighborhood of the seed pixel may be searched. Merely by way of example, 8 pixels may be searched in the M×N×Q neighborhood of the seed pixel. As another example, 4 pixels may be searched in the M×N×Q neighborhood of the seed pixel.

In 730, a judgment may be made as to whether there is a pixel marked as A in the M×N×Q neighborhood of the seed pixel. According to the example already described, a pixel may be assigned to mark A when its gray value is less than the average gray value (see 630). If there is a pixel that is assigned mark A in the M×N×Q neighborhood of the seed pixel, 740 may be performed. Otherwise, 750 may be performed.

In 740, the pixel in the M×N×Q neighborhood of the seed pixel and assigned mark A may be recorded as a boundary pixel. The boundary pixel may be located on the boundary of region of interest.

In 750, the pixel in M×N×Q neighborhood of seed pixel may be recorded as an internal pixel. The internal pixel may be located inside the region of interest.

In 760, a judgment may be made as to whether there is a pixel that is assigned mark B in the M×N×Q neighborhood of the seed pixel and has not been recorded either as an internal pixel or a boundary pixel. As described above with reference to 630, a pixel is assigned mark B when its gray value is not less than the average gray value. If there is a pixel in the M×N×Q neighborhood of the seed pixel that is assigned mark B and has not be recorded either as an internal pixel or a boundary pixel, 780 may be performed. Otherwise, 770 may be performed.

In 770, the search for a pixel in the M×N×Q neighborhood of the seed pixel may be finished.

In 780, the pixel in the M×N×Q neighborhood of the seed pixel that is marked as B and has not be recorded may be designated as a seed pixel. The operations in 720 to 770 may be repeated until all pixels in the M×N×Q neighborhood of the seed pixel have been recorded and the search may terminate.

Process 700 may identify one or more boundary pixels in the projection image. The boundary of a region of interest may be determined by connecting adjacent boundary pixels. In some embodiments, the boundary of the region of interest may be a maximum boundary connecting adjacent boundary pixels. For instance, if there are more than one way of connecting two adjacent boundary pixels, the shortest connection may be designated as the section of boundary connecting the two adjacent boundary pixels. As another example, if there are more than one way of connecting two adjacent boundary pixels, the connection whose resultant region of interest has a largest area may be designated as the section of boundary connecting the two adjacent boundary pixels.

In some embodiments, a projection image in process 700 may be a mammary gland projection image. A boundary of the mammary gland in a projection image may be determined by performing process 700.

It should be noted that process 700 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. In some embodiments, any number of seed pixels (e.g., 3, 5, 10, etc.) may be determined from one or more pixels of a projection image.

Figure 8:
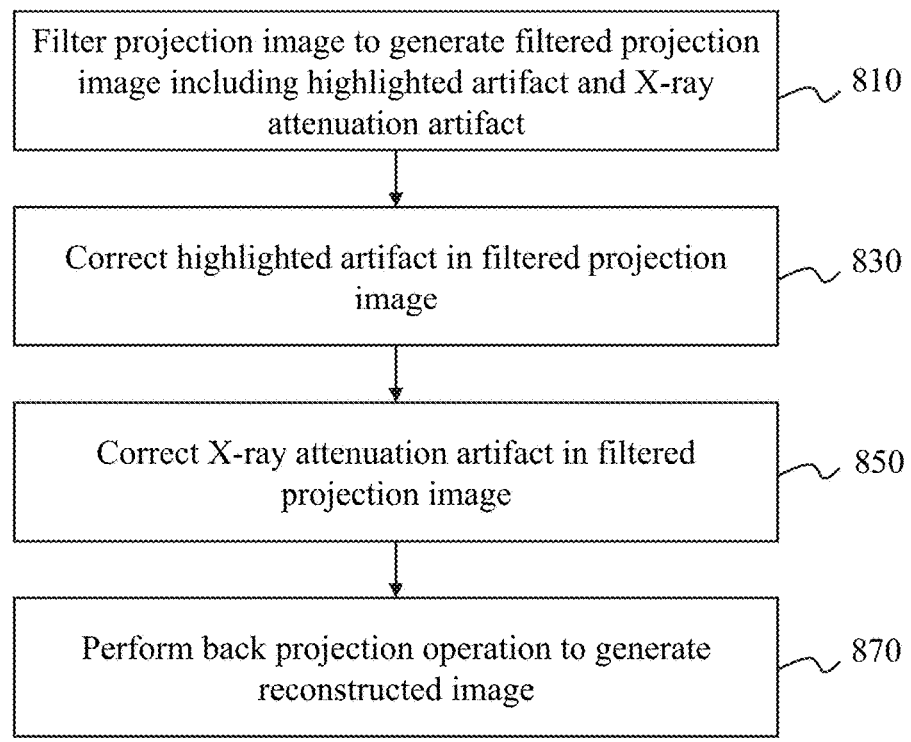
FIG. 8 is a flowchart illustrating an exemplary process for generating a reconstructed image in accordance with some embodiments of the present disclosure.

FIG. 8 is a flowchart illustrating an exemplary process 800 for generating a reconstructed image in accordance with some embodiments of the present disclosure. Process 800 may also be referred to as filtered back projection. In some embodiments, process 800 may be performed by reconstruction module 330 of imaging processing device 120 shown in FIG. 3A and FIG. 3C. In some embodiments, process 800 described with reference to FIG. 8 may be an exemplary process for achieving 440 shown in FIG. 4.

In 810, a projection image from one or more projection angles may be filtered to generate a filtered projection image. Filtered projection image generation operation in 810 may be performed by filtered projection image generation unit 331 of FIG. 3C. The projection image may be filtered according to a filter algorithm. The filter algorithm may include the Ramp-Lak filter algorithm, the Shepp-Logan filter algorithm, the Hamming filter algorithm, or the like, or a combination thereof. In some embodiments, the filtered projection image may include artifact such as a highlighted artifact, an X-ray attenuation artifact, a detector edge artifact, a mammary edge artifact, a serrated artifact, or the like, or a combination thereof.

In 830, the highlighted artifact in the filtered projection image may be corrected. Highlighted artifact correction operation in 830 may be performed by artifact correction unit 333 of FIG. 3C. The highlighted artifact may take the form of a highlight edge around the projection object in a projection image. The highlighted artifact may be caused by filtering.

In 850, an X-ray attenuation artifact in the filtered projection image may be corrected. X-ray attenuation artifact correction operation in 850 may be performed by artifact correction unit 333 of FIG. 3C. The X-ray attenuation artifact may be caused by difference in activities between X-ray photons. As described with reference to FIG. 2, radiation emitted by radiation source 201 may pass through a projection object and reach detector 203 to generate a projection image on detector 203. As X-ray passes through the projection object, low energy X-ray photons may be attenuated more, and the remaining high energy photons may be attenuated less than low energy photons. Such a difference in photon attenuation may cause X-ray attenuation artifact in the projection image.

In 870, a reconstructed image may be generated by performing a back projection operation on the filtered projection image. Back projection operation in 870 may be performed by back projection unit 335 of FIG. 3C. The reconstructed image may include one or more tomographic images. Back projection may be performed based on the inverse transformation of each view through a filtered projection image in the direction it was originally acquired. As used herein, "view" may refer to an angle at which a projection image is obtained.

In some embodiments, the projection image in process 800 may be a mammary gland projection image. The reconstructed image may be a reconstructed mammary gland projection image. A plurality of mammary gland projection images may be processed based on the filtered back projection operation to generate a reconstructed mammary gland projection image.

It should be noted that process 800 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. In some embodiments, some steps may be omitted or added. For example, 830 or 850 may be omitted. In some embodiments, 810, 830, and 850 may be performed in any order. For example, 830 and 850 may be performed at the same time. As another example, 850 may be performed before 830. As a further example, 830 and/or 850 may be performed before 810. In some embodiments, the projection object may be an organism, and an organ (e.g., a mammary gland, a hand, a head, a lung, etc.), or the like, or a combination thereof.

Figure 9:
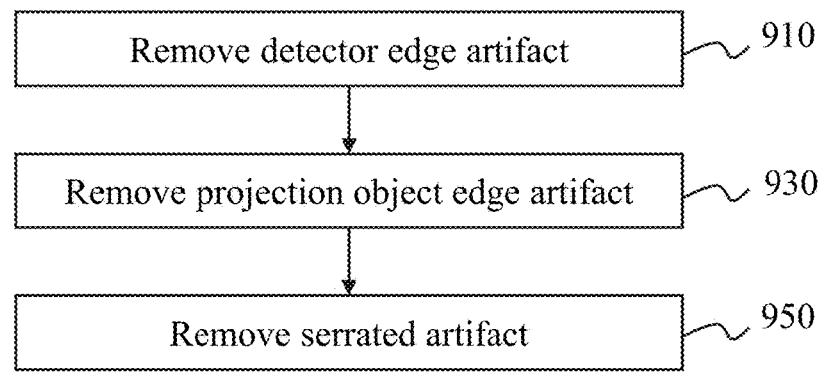
FIG. 9 is a flowchart illustrating an exemplary process for removing artifact in a reconstructed image in accordance with some embodiments of the present disclosure.

FIG. 9 is a flowchart illustrating an exemplary process 900 for removing artifact in a reconstructed image in accordance with some embodiments of the present disclosure. In some embodiments, process 900 may be performed by artifact removal module 340 of imaging processing device 120 shown in FIG. 3A and FIG. 3D. In some embodiments, process 900 described with reference to FIG. 9 may be an exemplary process for achieving 450 shown in FIG. 4.

In 910, a detector edge artifact may be removed. The artifact removal in 910 may be performed by detector edge artifact removal unit 341. More descriptions regarding a detector edge artifact may be found elsewhere in the present disclosure. See, for example, FIG. 3A and the description thereof.

The detector edge artifact may be removed by setting the gray values of the pixels in a detector edge artifact based on the gray values of pixels in the neighborhood of the area of a detector edge artifact. In some embodiments, the process for removing a detector edge error may include one or more of the following operations. The neighborhood area of a detector edge artifact may be determined. The neighborhood area may be an area close to the detector edge artifact and outside of the detector edge artifact. The neighborhood area may be an area of any size or shape. The average gray value of the pixels in the neighborhood area may be determined. In some embodiments, the pixels in the detector edge artifact in the tomographic image (e.g., a same slice of a CT image, etc.) may be assigned a same gray value. For instance, the gray values of the pixels in the detector edge artifact may be assigned the average gray value of pixels in the neighborhood area.

In 930, a projection object edge artifact may be removed. In some embodiments, the projection object may include a mammary gland. In some embodiments, the projection object edge may include the edge of the mammary gland. In some embodiments, the process for removing a mammary gland edge artifact may include one or more of the following operations. The boundary of the projection object in one or more projection images from one or more views may be determined by an edge detection algorithm. The edge detection algorithm may include, for example, the Sobel edge detection algorithm, the Canny edge detection algorithm, a phase congruency-based algorithm, the Otsu's algorithm, or the like, or a combination thereof. For example, the boundary of a projection object may be detected by the Otsu's algorithm first and then by the Sobel edge detection algorithm. A 3D projection object surface may be generated based on one or more projection images from one or more views using a simultaneous algebraic reconstruction technique (SART). The pixel value distribution of each projection image from a projection view may be updated based on the boundary of a projection image. The gray value of the pixels outside of the region of the projection object may be set as 0 after each iteration in SART. A pixel may be determined to be outside of the region of the projection object based on the 3D projection object surface.

In some embodiments, the projection object may be a mammary gland. The artifact removal in 930 may be performed by mammary gland edge artifact removal unit 343.

In 950, a serrated artifact may be removed. The artifact removal in 950 may be performed by serrated artifact removal unit 345 shown in FIG. 3A. More descriptions regarding a serrated artifact removal method may be found elsewhere in the present disclosure. See, for example, FIG. 10 and FIG. 11, and the description thereof.

It should be noted that process 900 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. In some embodiments, some steps may be reduced or added. For example, 930 may be omitted. In some embodiments, 930 and 910 may be performed at the same time. In some embodiments, 930 may be performed before 910. In some embodiments, one or more steps may be added to remove one or more other artifacts including, for example, an artifact caused by the movement of the patient, metal worn by the patient when the patient is scanned, the arcing of the radiation source (e.g., a bulb, etc.), a deviation of the detector from its normal operation condition, or the like, or a combination thereof. In some embodiments, the projection object may be an organism, and an organ (e.g., a mammary gland, a hand, a head, a lung, etc.), or the like, or a combination thereof.

Figure 10:
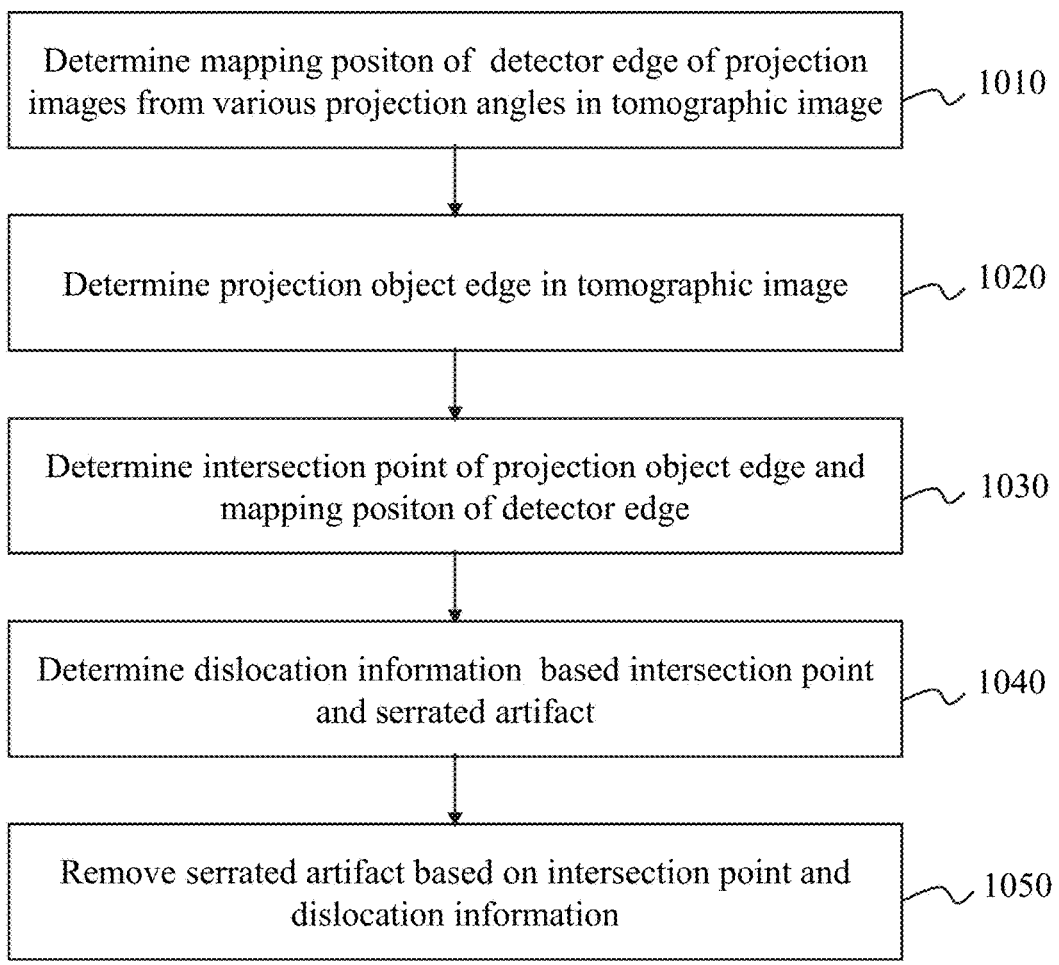
FIG. 10 is a flowchart illustrating an exemplary process for removing serrated artifact in accordance with some embodiments of the present disclosure.

FIG. 10 is a flowchart illustrating an exemplary process 1000 for removing serrated artifact in accordance with some embodiments of the present disclosure. In some embodiments, process 1000 may be performed by serrated artifact removal unit 345 of imaging processing device 120 shown in FIG. 3A. In some embodiments, process 1000 described with reference to FIG. 10 may be an exemplary process for achieving 950 as shown in FIG. 9.

Figure 13:
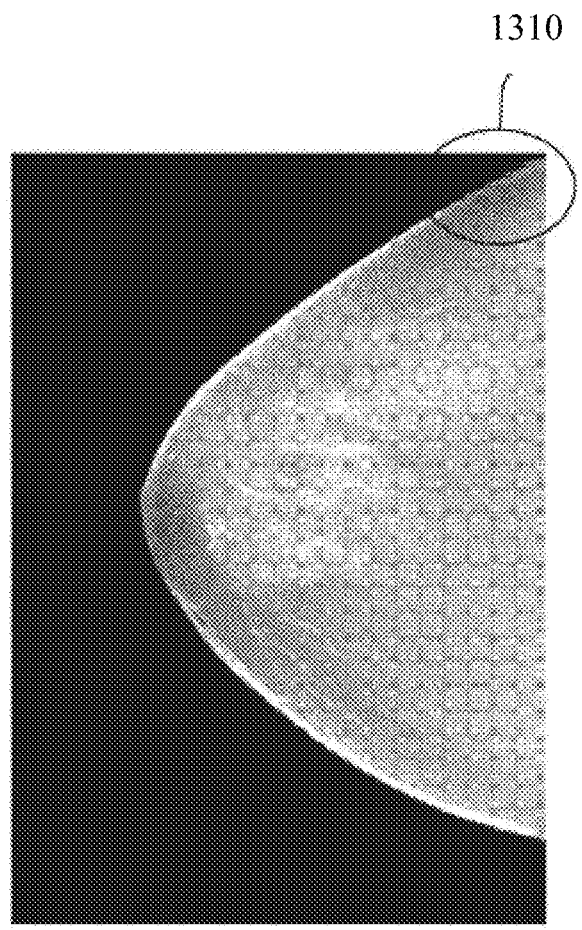
FIG. 13 illustrates an exemplary reconstructed image of a mammary gland.

In some embodiments, a serrated artifact may be present in a reconstructed image. FIG. 13 illustrates a mammary gland reconstructed image. As shown in FIG. 13, serrated artifacts are present in region 1310. FIG. 14 illustrates a mammary gland reconstructed image without serrated artifact correction. As shown in FIG. 14, serrated artifacts are present in area 1410 and 1420. The mammary gland reconstructed image shown in FIG. 15A and FIG. 15B includes serrated artifact S (e.g., S1, S2, S3, S4, S1', S2', S3', S4').

Figure 15A:
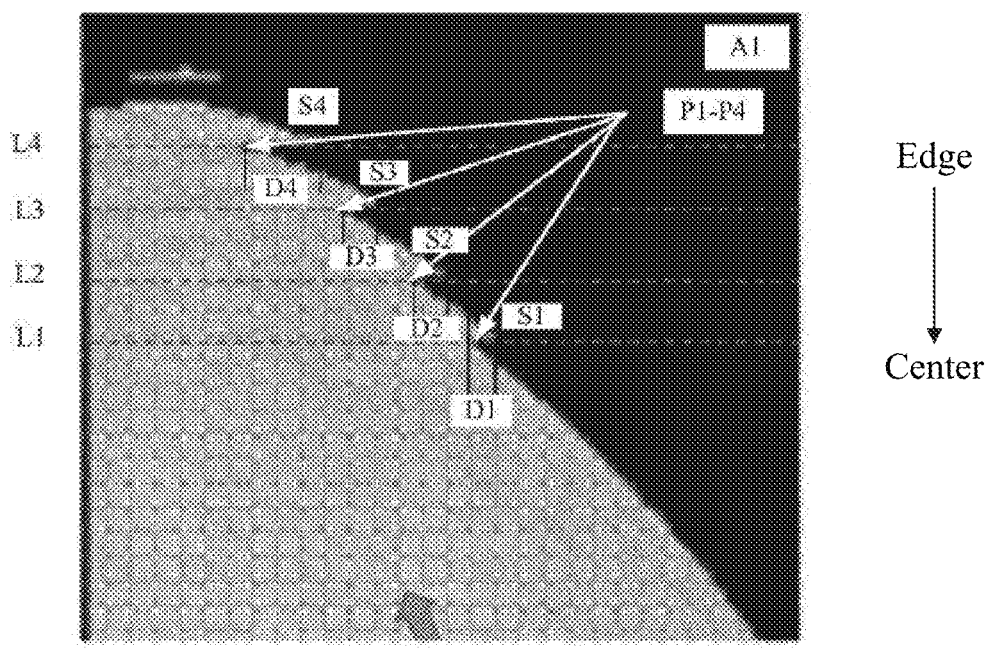
FIG. 15A and FIG. 15B illustrate exemplary reconstructed images of a mammary gland with serrated artifacts.
Figure 15B:
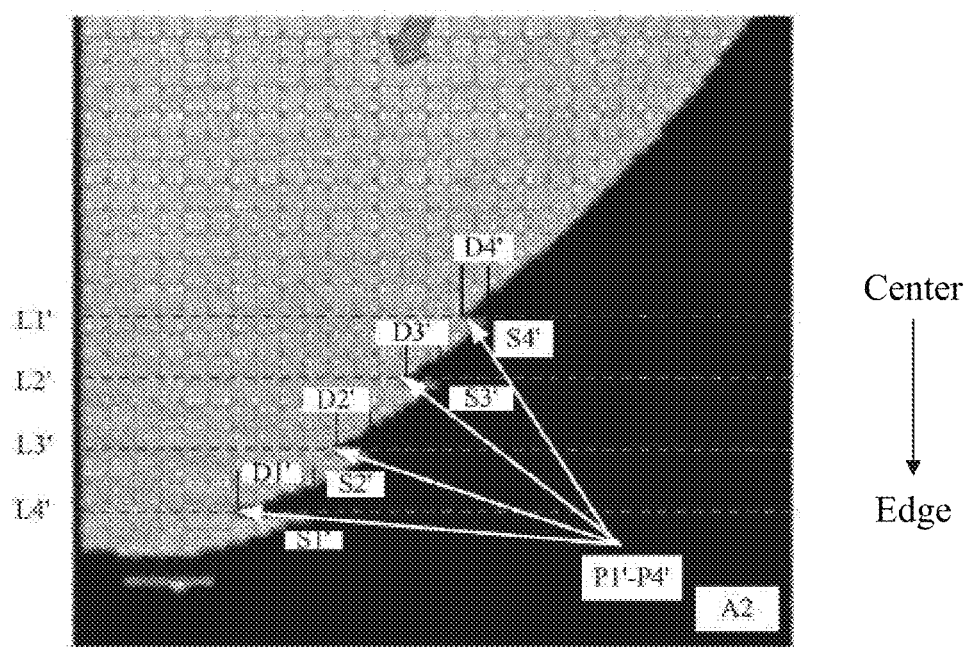

In 1010, the mapping position of the detector edge in a projection image from a projection view with respect to the detector edge in a corresponding tomographic image may be determined. A tomographic image may be part of a reconstructed image. The reconstructed image may include one or more tomographic images. A tomographic image may depict a layer of the projection object. In some embodiment, a tomographic image may be a mammary gland tomographic image that may depict a layer of the mammary gland. FIG. 15A depicts an upper portion of a mammary gland and FIG. 15B depicts a lower portion of the mammary gland. Horizontal dotted lines L1-L4 and L1'-L4' depict mapping positions of the detector edge.

In some embodiments, 1010 may include one or more of the following operations. A first geometric position relationship between radiation source 201 and detector 203 (shown in FIG. 2A) may be determined. A second geometric position relationship between a projection image from a projection view and a corresponding tomographic image may be determined. The mapping coordinates of a pixel in the projection image with respect to the corresponding pixel in the corresponding tomographic image may be determined based on the first geometric position relationship and the second geometric position relationship. As used herein, a pixel in a projection image and the corresponding pixel in a corresponding tomographic image may relate to a same portion (e.g., a same spot, etc.) of the projection object. The mapping coordinates of a pixel in the projection image with respect to the corresponding pixel in the tomographic image may be determined utilizing, for example, an image interpolation algorithm, a bilinear interpolation algorithm, a recent field interpolation algorithm, or the like, or a combination thereof. According to a bilinear interpolation algorithm, the mapping coordinates of a pixel may be determined based on the coordinates of two neighboring pixels. In a recent field interpolation algorithm, the mapping coordinates of a pixel may be determined based on the coordinates of a neighboring pixel closest to the pixel. The mapping position of the detector edge in the projection image with respect to the detector edge in the corresponding tomographic image may be determined based on an imaging area of the detector in the projection image and the mapping coordinates of the pixels of the detector edge in the projection image.

For example, the resolution of a projection image may be 1000*1000. The mapping coordinates of a pixel in the projection image with respect to the corresponding pixel in the corresponding tomographic image may be smaller than 0 or larger than 1000. A pixel whose mapping coordinates are smaller than 0 or larger than 1000 may be a pixel outside of the imaging area of the detector. The detector edge may be determined by a critical value (e.g., 0 and 1000). As shown in FIG. 15A and FIG. 15B, line L (e.g., L1, L2, L3, L4, L1', L2', L3' and L4') includes the mapping position corresponding to the detector edge. In some embodiments, a point (x, y) on the line L may be described in a two-dimensional array. For example, (1, 2) may describe a point with a horizontal coordinate of 1 and a vertical coordinate of 2 on the line L.

In 1020, a projection object edge in the tomographic image may be determined. The projection object edge may be a boundary between an area of projection object and a direct exposing area. As used herein, a direct exposing area may refer to an area of air (e.g., an area outside of a projection object, etc.).

In some embodiments, a projection object may be a mammary gland. The mammary gland edge in a tomographic image may be the boundary between region of the mammary gland and a region outside of the mammary gland (i.e., a direct exposing area). For example, as shown in FIG. 15A, the gray area may depict a region corresponding to a mammary gland (i.e., a region of mammary gland), and the dark area may depict the region outside of the mammary gland (i.e., a direct exposing area). There is a boundary with a serrated line between the gray area and the dark area. The mammary gland edge may be the boundary between the gray area and the dark area.

In 1030, an intersection point corresponding to the projection object edge and the mapping position corresponding to the detector edge may be determined.

As shown in FIG. 15A, Point P (e.g., P1, P2, P3, and P4) is an intersection point corresponding to the mammary gland edge (the boundary between the gray area and the dark area) and the mapping position corresponding to the detector edge (the horizontal dotted lines L1, L2, L3, and L4). Artifact S (e.g., S1, S2, S3, and S4) has a shape of serrations, and referred to as a serrated artifact. Point P1, P2, P3, and P4 may be roughly horizontal to serrated artifact S1, S2, S3, and S4.

In 1040, dislocation information of each intersection point may be determined based on the intersection point and the mapping position of the detector edge. The dislocation information may be a distance between the intersection point and an edge point of a corresponding serrated artifact. The corresponding serrated artifact may be the serrated artifact that is roughly horizontal to the intersection point.

For example, in FIG. 15A, the corresponding serrated artifact of intersection point P1 may be serrated artifact S1. Dislocation information of the intersection point P1 may be the distance between the intersection point P1 and the edge point of the serrated artifact S1, which is denoted as D1.

In 1050, the serrated artifact may be removed based on the intersection point and the dislocation information. The serrated artifact may be removed by moving its edge for a distance towards the region of the projection object (e.g., a mammary gland, etc.).

In some embodiments, the distance may be equal to the dislocation information of the intersection point. In some embodiments, the distance may be a statistic value determined based on the dislocation information of a plurality of intersection points. For example, the distance may be the average value of the dislocation information of one or more intersection points in the reconstructed image. As another example, the distance may be the median value of the dislocation information of one or more intersection points in the reconstructed image.

In some embodiments, as shown in FIG. 15A, serrated artifact S1 may be removed by moving its edge toward the region of the mammary gland (the gray area) for a distance equal to the dislocation information of intersection point P1. More descriptions regarding the method to remove serrated artifact based on intersection point and the corresponding dislocation information may be found elsewhere in the present disclosure. See, for example, FIG. 11 and the description thereof.

It should be noted that process 1000 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure. In some embodiments, 1010 and 1020 may be performed at the same time. In some embodiments, 1020 may be performed before 1010. In some embodiments, the projection object may be an organism, and an organ (e.g., a mammary gland, a hand, a head, a lung, etc.), or the like, or a combination thereof.

Figure 11:
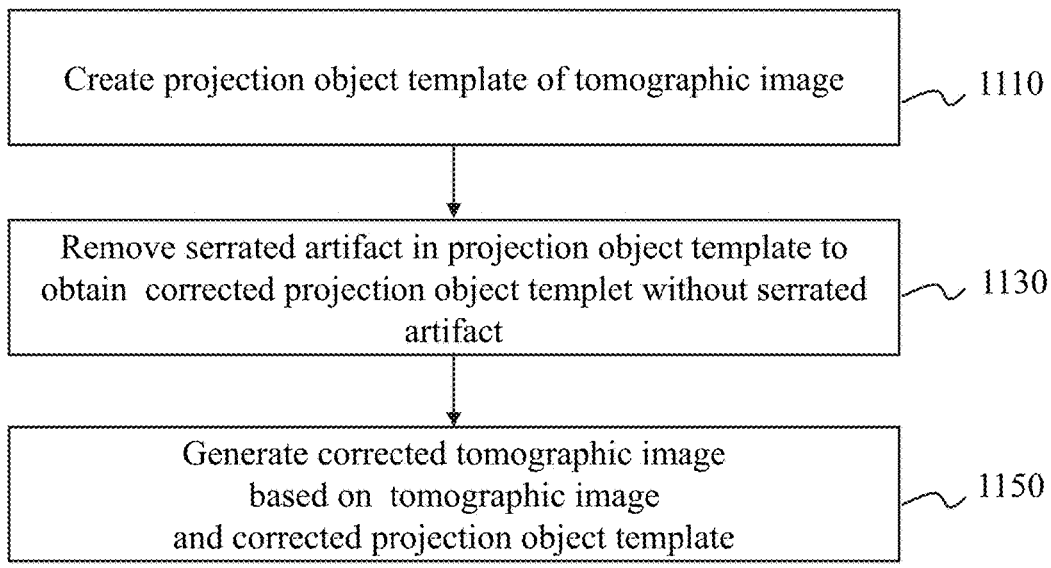
FIG. 11 is a flowchart illustrating an exemplary process for removing serrated artifact in accordance with some embodiments of the present disclosure.

FIG. 11 is a flowchart illustrating an exemplary process 1100 for removing a serrated artifact based on an intersection point and relevant dislocation information in accordance with some embodiments of the present disclosure. In some embodiments, process 1100 may be performed by serrated artifact removal unit 345 in imaging processing device 120 as shown in FIG. 3A. In some embodiments, process 1100 described with reference to FIG. 11 may be an exemplary process for achieving 1050 as shown in FIG. 10.

In 1110, a projection object template of a tomographic image may be generated. The projection object template may reduce image processing cost. The projection object template may be generated by setting gray values of pixels in a number of different regions of the tomographic image. In some embodiments, the tomographic image may have two different regions (e.g., a projection object region and a direct exposing region) and a binary projection object template may be used. For example, the gray value of pixels in the projection object region may be set to E, and the gray value of pixels out of the direct exposing region may be set to F. For example, E may be 1 and F may be 0. In some embodiments, the tomographic image may have more than two different regions and a multi-value projection object template may be used. For example, the tomographic image may have three different regions (e.g., a soft tissue region, a bone region, and a direct exposing region) and a three-value projection object template may be used. The number of different regions may be any integer (e.g., one, two, three, four, etc.).

Figure 16A:
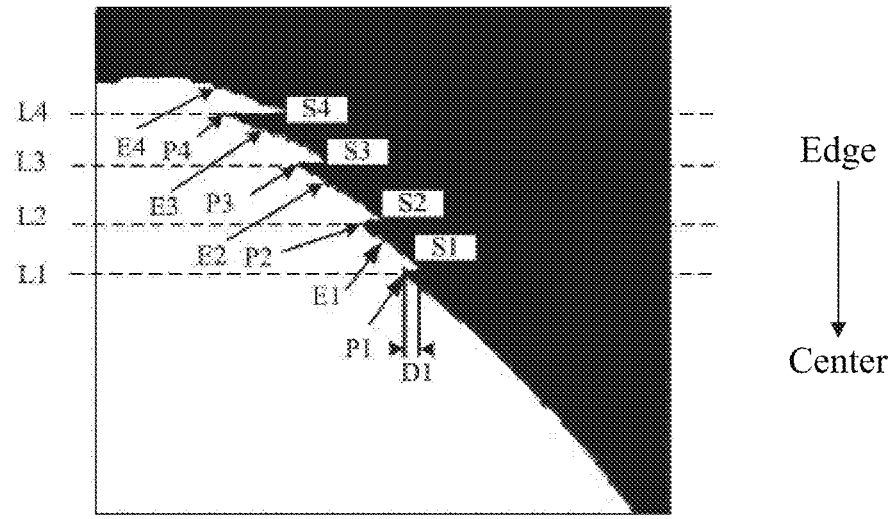
FIG. 16A to FIG. 16D illustrate exemplary mammary gland templates.

In some embodiments, a projection object may be a mammary gland and a mammary gland template may be used. As shown in FIG. 16A, the gray values of the pixels in a region of the mammary gland may be set as 1, and the gray values of the pixels in a direct exposing region may be set as 0. In that way, the region of the mammary gland may be depicted as white, and the direct exposing region may be depicted as black.

In 1130, a serrated artifact in the projection object template may be removed to obtain a corrected projection object templet without the serrated artifact. The serrated artifact may be removed in any order. In some embodiments, the serrated artifact in the portion of the template corresponding to the region of a projection object close to the center of the projection object may be removed first and the serrated artifact in the portion of the template corresponding to the region of the projection object close to an edge of the projection object may be removed afterwards.

In some embodiments, the serrated artifact in the portion of the template corresponding to the region of a projection object close to the edge of the projection object may be removed first and the serrated artifact in the portion of the template corresponding to the region of a projection object close to the center of the projection object may be removed afterwards.

Figure 16B:
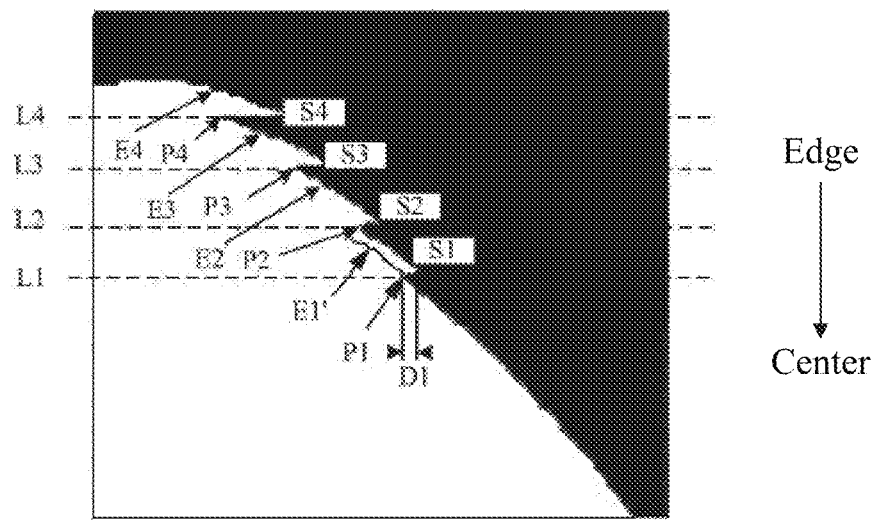

In some embodiments, a projection object may be a mammary gland and a mammary gland template may be used. As shown in FIG. 16A and FIG. 16B, S (e.g., S1, S2, S3, S4, S1', S2', S3' and S4') may be a serrated artifact and E (e.g., E1, E2, E3 and E4) may be an edge of the serrated artifact. L (e.g., L1, L2, L3 and L4) may be the mapping position corresponding to the detector edge. P (e.g., P1, P2, P3 and P4) may be an intersection point corresponding to a mammary gland edge (e.g., a boundary between the gray area and the dark area). D (e.g., D1, D2, D3 and D4) may be dislocation information of the corresponding intersection point.

Serrated artifact S1 to S4 in FIG. 16A may be removed in any order (e.g., in a successive order from S1 to S4, in a reversed order from S4 to S1, etc.). Merely by way of example, serrated artifact S1 may be removed first and then S2, S3, and S4 may be removed successively. Serrated artifact S1 may be removed by moving its edge E1 towards the portion of the image corresponding to the center of mammary gland that is on the left side of E1 in FIG. 16A for distance D1. The moved edge of serrated artifact is E1' shown in FIG. 16B. The gray value of the pixels in the area between E1 and E1' may be set as 0 so that the area between E1 and E1' may be black (See FIG. 16C). In that way, serrated artifact S1 may be removed to obtain a corrected mammary gland edge without serrated artifact S1.

Figure 16C:
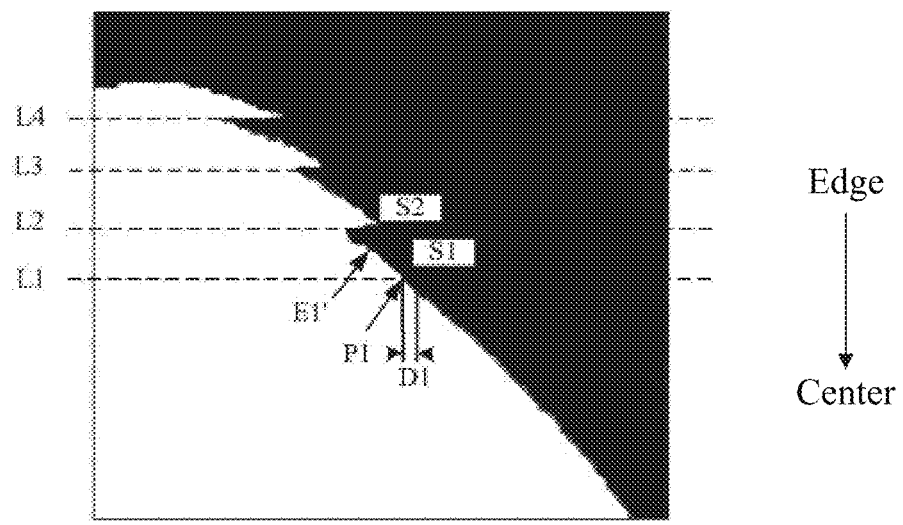
Figure 16D:
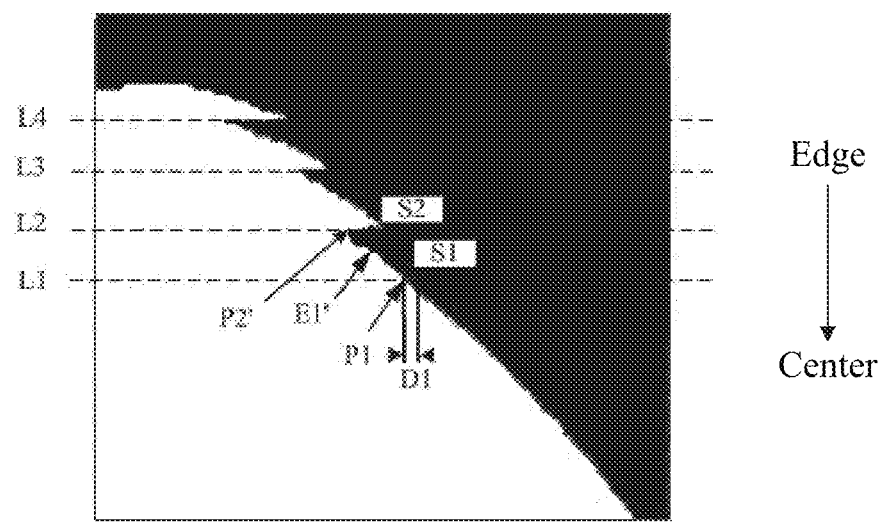

A boundary between the light area and the dark area in FIG. 16C may depict a corrected mammary gland edge after removing serrated artifact S1. The determination of an intersection point between the corrected mammary gland edge and the mapping position corresponding to the detector edge may be repeated. As shown in FIG. 16D, P2' is an intersection point corresponding to a corrected mammary gland edge and a mapping position corresponding to detector edge L2. Serrated artifact S2 to S4 may be successively removed using the same way of removing serrated artifact S1.

In 1150, a corrected tomographic image may be generated based on the tomographic image and the corrected projection object template in which the serrated artifact is removed (or referred to as without the serrated artifact). According to the corrected projection object template, a corrected region outside of the projection object (a dark area in the corrected projection object template) may be obtained. The gray value of the pixels in the corresponding region outside of the projection objection in a tomographic image may be set as 0. In that way, the serrated artifact in the tomographic image may be removed to generate a corrected tomographic image. A projection object edge may be smooth or essentially smooth in the corrected tomographic image.

Figure 17:
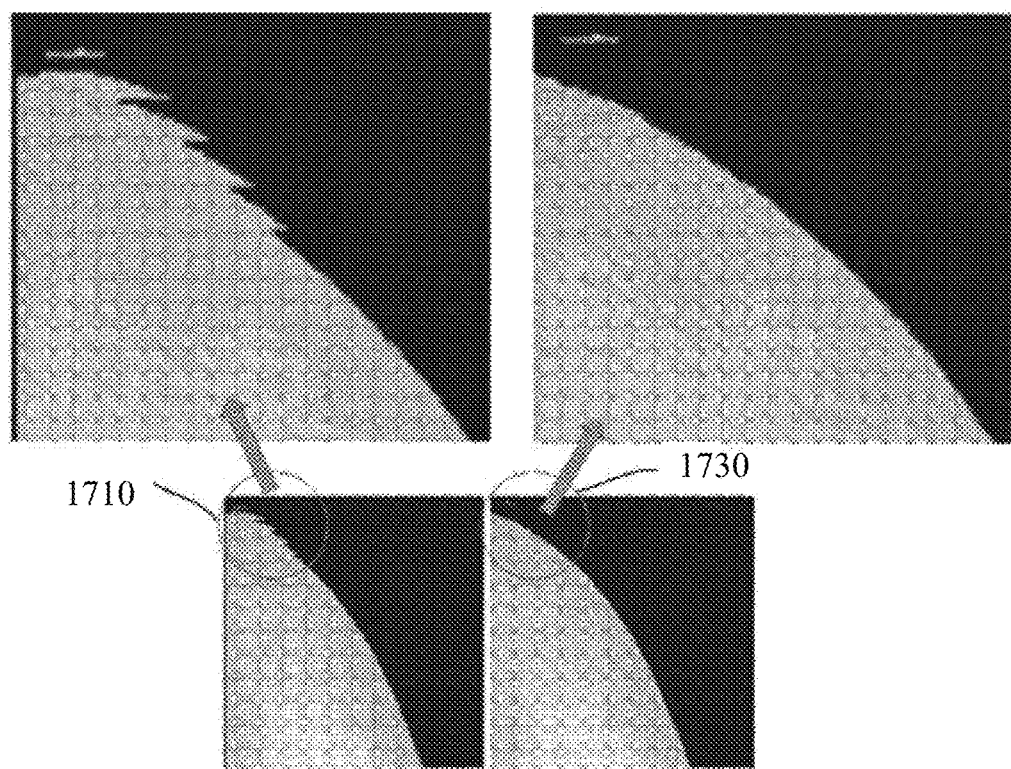
FIG. 17 illustrates exemplary mammary gland reconstructed images.

In some embodiments, the projection object may be a mammary gland. As shown in FIG. 17, there are serrated artifacts in mammary gland edge in area 1710 before serrated artifacts are removed, and there is no visible serrated artifact along the mammary gland edge in area 1730 after serrated artifacts are removed. In some embodiments, the projection object may be an organism, and an organ (e.g., a mammary gland, a hand, a head, a lung, etc.), or the like, or a combination thereof.

EXAMPLES

The following examples are provided for illustration purposes, and not intended to limit the scope of the present disclosure.

Example 1

Figure 12:
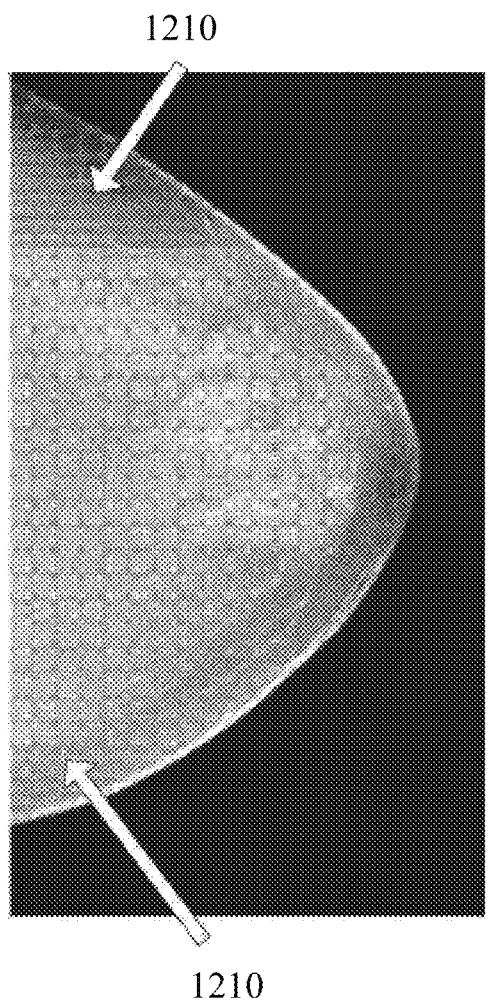
FIG. 12 illustrates a reconstructed image of a mammary gland.

FIG. 12 illustrates a reconstructed image of a mammary gland. As shown in FIG. 12, there are detector edge artifacts in region 1210. The detector edge artifacts are strip-shaped. The existence of the detector edge artifacts may influence the results of a diagnosis. In some embodiments, the detector edge artifacts may be removed according to process 900 described with reference to FIG. 9.

Example 2

FIG. 13 illustrates an exemplary reconstructed image of a mammary gland. As shown in FIG. 13, there are serrated artifacts in region 1310. The existence of the serrated artifacts may influence the result of a diagnosis. In some embodiments, the serrated artifacts may be removed according to process 1000 and process 1100 described with reference to FIG. 10 and FIG. 11.

Example 3

FIG. 14 illustrates an exemplary reconstructed image of mammary gland without serrated artifact correction. As shown in FIG. 14, the top portion of FIG. 14 depicts an upper portion of a mammary gland, and the bottom portion of FIG. 14 depicts a lower portion of the mammary gland. There are serrated artifacts in region 1410 (at the upper edge of the mammary gland reconstructed image) and region 1420 (at the bottom edge of the mammary gland reconstructed image).

Example 4

FIG. 15A and FIG. 15B illustrate reconstructed images of a mammary gland with serrated artifacts. FIG. 15A depicts an upper portion of a mammary gland. FIG. 15B depicts a lower portion of the mammary gland. Serrated artifact (e.g., S1, S2, S3, S4, S1', S2', S3' and S4') is serration-shaped. Line L (e.g., L1, L2, L3, L4, L1', L2', L3' and L4') is a mapping position corresponding to the detector edge. Point P (e.g., P1, P2, P3, P4, P1', P2', P3' and P4') is an intersection point corresponding to a mammary gland edge (a boundary between the gray area and the dark area) and line L. D (e.g., D1, D2, D3, D4, D1', D2', D3' and D4') is dislocation information of intersection point P, which is the distance between intersection point P and the edge point of a corresponding serrated artifact.

Example 5

FIG. 16A to FIG. 16D illustrate exemplary mammary gland templates. FIG. 16A and FIG. 16B illustrate mammary gland templates before serrated artifact were removed. FIG. 16C and FIG. 16D illustrate mammary gland templates after serrated artifact S1 were removed. As shown in FIGS. 16A-16D, line L (e.g., L1, L2, L3, and L4) is a mapping position corresponding to the detector edge. P (e.g., P1, P2, P3, P4, and P2') is an intersection point corresponding to a mammary gland edge (a boundary between the gray area and the dark area) and line L. D (e.g., D1) is dislocation information of intersection point P, which is a distance between intersection point P and edge point of corresponding serrated artifact. E (e.g., E1, E2, E3, and E4) is an edge of the serrated artifact. E' (e.g., E1) is a corrected artifact edge which was obtained by moving edge E left for the distance equal to dislocation information of the corresponding intersection point P. For example, E1' was obtained by moving E1 left for the distance of D1. P' (e.g., P2') is an intersection point of line L and a corrected mammary gland edge after serrated artifact was removed.

Example 6

FIG. 17 illustrates exemplary mammary gland reconstructed images. The left portion of FIG. 17 was generated before serrated artifacts were removed. The right portion of FIG. 17 was generated after serrated artifacts were removed. As shown in FIG. 17, there are serrated artifacts along the mammary gland edge in area 1710 before serrated artifacts were removed, and there is no visible serrated artifact in the mammary gland edge in area 1730 after serrated artifacts were removed.

Example 7

Figure 18:
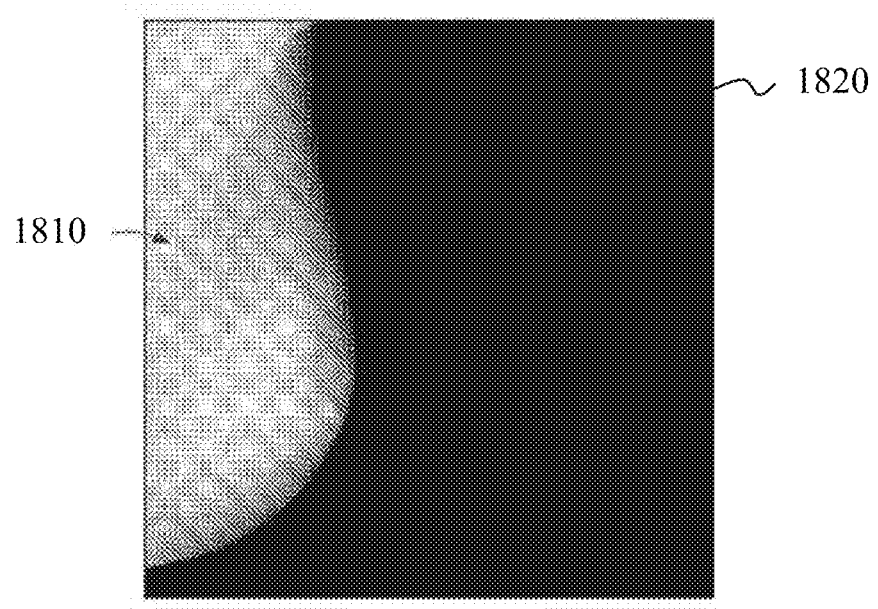
FIG. 18 illustrates an exemplary projection image of a mammary gland.

FIG. 18 illustrates an exemplary projection image of a mammary gland. FIG. 18 may be generated by imaging device 110 according to some embodiments of the present disclosure. As shown in FIG. 18, the mammary gland in area 1810 has a higher gray value than the right portion of the projection image. The right portion of the projection image denoted as area 1820 is the background with a lower gray value than the left portion of the projection image.

Example 8

FIG. 19 illustrates a process for generating a segmented region by merging a plurality of regions of interest according to some embodiments of the present disclosure. As shown in FIG. 19, a1, a2, and a3 are three regions of interest, and b is a region generated by overlaying a1, a2, and a3. C is a segmented region, which is a union of a1, a2, and a3.

Example 9

FIG. 20 illustrates a process for generating a segmented region based on a rectangular segmenting algorithm according to some embodiments of the present disclosure. As shown in FIG. 19, the gray area is a region of a mammary gland that is a region of interest. The segmented region may be rectangle S whose diagonal vertexes are M $(X_1, Y_1)$ and N $(X_2, Y_2)$. $X_1$ is the largest horizontal ordinate value of all pixels in a plurality of regions of interest. $Y_1$ is the smallest longitudinal ordinate value of all pixels in the plurality of regions of interest. $X_2$ is the smallest horizontal ordinate value of all pixels in the plurality of regions of interest. $Y_1$ is the largest longitudinal ordinate value of all pixels in the plurality of regions of interest.

Example 10

FIG. 21 illustrates an exemplary reconstructed image of a mammary gland. As shown in FIG. 21, there are mammary gland edge artifacts in area 2110 and area 2130.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method comprising:
   obtaining a projection image of a projection object, the projection image being acquired by an imaging device, the imaging device including a radiation source and a detector;
   pre-processing, by a processor, the projection image to generate a processed projection image; and
   reconstructing, by the processor, the processed projection image to generate a reconstructed image;
   the pre-processing the projection image including segmenting a region of interest in the projection image to generate a segmented projection image, and the segmenting the region of interest in the projection image including:
      determining, among one or more pixels of the projection image, one or more pixels related to the region of interest based on a gray value of each of the one or more pixels of the projection image; and
      determining a boundary of the region of interest based at least in part on the one or more pixels related to the region of interest, and the reconstructing the processed projection image to
generate the reconstructed image including:
filtering the processed projection image to generate a
filtered projection image; and
performing back projection to generate the reconstructed image based on the filtered projection image.

2. The method of claim 1, the pre-processing the projection image further including:
generating a negative film of the segmented projection image; and
correcting a geometrical error of the negative film of the segmented projection image to generate the processed projection image.

3. The method of claim 1, wherein the filtered projection image includes at least one of a highlighted artifact or an X-ray attenuation artifact, and the performing back projection to generate the reconstructed image based on the filtered projection image further includes:
correcting the at least one of the highlighted artifact or the X-ray attenuation artifact in the filtered projection image to generate a first image; and
performing back projection to generate the reconstructed image based on the first image.

4. The method of claim 1, the reconstructed image including an artifact, the method further comprising removing the artifact in the reconstructed image, the artifact including at least one of a detector edge artifact relating to a detector edge of the detector, a projection object edge artifact relating to a projection object edge, or a serrated artifact, and the removing the artifact in the reconstructed image including at least one of:
removing the detector edge artifact;
removing the projection object edge artifact; or
removing the serrated artifact.

5. The method of claim 4, the reconstructed image including a tomographic image, and the removing serrated artifact including:
determining a mapping position of the detector edge in the tomographic image;
determining the projection object edge in the tomographic image;
determining an intersection point corresponding to the projection object edge and the mapping position of the detector edge;
determining dislocation information of the intersection point based on the intersection point and the serrated artifact; and
removing the serrated artifact based on the intersection point and the dislocation information of the intersection point.

6. The method of claim 5, the determining a mapping position of the detector edge in the tomographic image including:
determining a first geometric position relationship between the radiation source and the detector;
determining a second geometric position relationship between the projection image and the tomographic image;
determining mapping coordinates of pixels in the projection image based on the first geometric position relationship and the second geometric position relationship; and
determining the mapping position of the detector edge based on the mapping coordinates of pixels in the projection image and an imaging area of the detector in the projection image.

7. The method of claim 5, the dislocation information of the intersection point is a horizontal distance between the intersection point and a point on an edge of the serrated artifact.

8. The method of claim 5, the removing the serrated artifact based on the intersection point and the dislocation information of the intersection point including:
creating a projection object template of the tomographic image;
removing the serrated artifact in the projection object template to obtain a corrected projection object template; and
removing the serrated artifact in the tomographic image based on the corrected projection object template.

9. The method of claim 1, the determining one or more pixels related to the region of interest comprising:
determining an average gray value of the one or more pixels of the projection image;
for each pixel of the one or more pixels of the projection image, assigning a first mark or a second mark to the pixel based on a relationship between a gray value of the pixel and the average gray value; and
designating one or more pixels having the first mark as the one or more pixels related to the region of interest.

10. The method of claim 1, the boundary of the region of interest is determined based on a seed filling algorithm.

11. A non-transitory computer readable medium comprising executable instructions that, when executed by at least one processor, cause the at least one processor to effectuate a method comprising:
obtaining a projection image of a projection object, the projection image being acquired by an imaging device, the imaging device including a radiation source and a detector;
pre-processing the projection image to generate a processed projection image; and
reconstructing the processed projection image to generate a reconstructed image; and
the pre-processing the projection image including segmenting a region of interest in the projection image to generate a segmented projection image, and the segmenting the region of interest in the projection image including:
determine, among one or more pixels of the projection image, one or more pixels related to the region of interest based on a gray value of each of the one or more pixels of the projection image; and
determining a boundary of the region of interest based at least in part on the one or more pixels related to the region of interest, and
the reconstructing the processed projection image to generate the reconstructed image including:
filtering the processed projection image to generate a filtered projection image; and
performing back projection to generate the reconstructed image based on the filtered projection image.

12. A system comprising:
at least one storage medium including a set of instructions for image processing;
at least one processor in communication with the at least one storage medium, wherein when executing the set of instructions, the at least one processor is configured to direct the system to:

obtain a projection image of a projection object, the projection image being acquired by an imaging device, the imaging device including a radiation source and a detector;

pre-process the projection image to generate a processed projection image; and reconstruct the processed projection image to generate a reconstructed image;

the pre-processing the projection image including segmenting a region of interest in the projection image to generate a segmented projection image and the segmenting the region of interest in the projection image including:

determining, among one or more pixels of the projection image, one or more pixels related to the region of interest based on a gray value of each of the one or more pixels of the projection image; and determining a boundary of the region of interest based at least in part on the one or more pixels related to the region of interest, and the reconstructing the processed projection image to generate the reconstructed image including:

filtering the processed projection image to generate a filtered projection image; and performing back projection to generate the reconstructed image based on the filtered projection image.

13. The system of claim 12, wherein to pre-process the projection image, the at least one processor is further configured to direct the system to:

generate a negative film of the segmented projection image; and correct a geometrical error of the negative film of the segmented projection image to generate the processed projection image.

14. The system of claim 12, wherein the filtered projection image includes at least one of a highlighted artifact or an X-ray attenuation artifact, and the performing back projection to generate the reconstructed image based on the filtered projection image further includes:

correcting the at least one of the highlighted artifact or the X-ray attenuation artifact in the filtered projection image to generate a first image; and performing back projection to generate the reconstructed image based on the first image.

15. The system of claim 12, wherein:

the reconstructed image includes an artifact, the at least one processor is further configured to direct the system to remove the artifact in the reconstructed image, the artifact includes at least one of a detector edge artifact relating to a detector edge of the detector, a projection object edge artifact relating to a projection object edge, and or a serrated artifact, and to remove the artifact in the reconstructed image, the at least one processor is further configured to direct the system to perform at least one of:

remove the detector edge artifact;

remove the projection object edge artifact; or remove the serrated artifact.

16. The system of claim 15, wherein the reconstructed image includes a tomographic image, and to remove the serrated artifact, the at least one processor is further configured to direct the system to:

determine a mapping position of the detector edge in the tomographic image;

determine the projection object edge in the tomographic image;

determine an intersection point corresponding to the projection object edge and the mapping position of the detector edge;

determine dislocation information of the intersection point based on the intersection point and the serrated artifact; and remove the serrated artifact based on the intersection point and the dislocation information of the intersection point.

17. The system of claim 16, wherein to determine a mapping position of the detector edge in the tomographic image, the at least one processor is further configured to direct the system to:

determine a first geometric position relationship between the radiation source and the detector;

determine a second geometric position relationship between the projection image and the tomographic image;

determine mapping coordinates of pixels in the projection image based on the first geometric position relationship and the second geometric position relationship; and determine the mapping position of the detector edge based on the mapping coordinates of pixels in the projection image and an imaging area of the detector in the projection image.

18. The system of claim 16, the dislocation information of the intersection point is a horizontal distance between the intersection point and a point on an edge of the serrated artifact.

19. The system of claim 16, wherein to remove the serrated artifact based on the intersection point and the dislocation information of the intersection point, the at least one processor is further configured to direct the system to:

create a projection object template of the tomographic image;

remove the serrated artifact in the projection object template to obtain a corrected projection object template; and remove the serrated artifact in the tomographic image based on the corrected projection object template.

20. The system of claim 12, wherein the determining one or more pixels related to the region of interest comprising:

determining an average gray value of the one or more pixels of the projection image;

for each pixel of the one or more pixels of the projection image, assigning a first mark or a second mark to the pixel based on a relationship between a gray value of the pixel and the average gray value; and designating one or more pixels having the first mark as the one or more pixels related to the region of interest.

* * * * *